(12) United States Patent
Parihar et al.

(10) Patent No.: US 9,782,219 B2
(45) Date of Patent: *Oct. 10, 2017

(54) ELECTROSURGICAL DEVICE WITH DISPOSABLE SHAFT HAVING CLAMSHELL COUPLING

(71) Applicant: Ethicon Endo-Surgery, LLC, Guaynabo, PR (US)

(72) Inventors: Shailendra K. Parihar, Mason, OH (US); David T. Martin, Milford, OH (US); William J. White, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,885

(22) Filed: Jul. 8, 2015

(65) Prior Publication Data

US 2015/0305804 A1 Oct. 29, 2015

Related U.S. Application Data

(63) Continuation of application No. 13/798,677, filed on Mar. 13, 2013, now Pat. No. 9,107,685.

(51) Int. Cl.
A61B 19/00 (2006.01)
A61B 18/14 (2006.01)
(Continued)

(52) U.S. Cl.
CPC .......... *A61B 18/1447* (2013.01); *A61B 17/28* (2013.01); *A61B 17/2804* (2013.01);
(Continued)

(58) Field of Classification Search
CPC ................ A61B 19/22; A61B 19/2203; A61B 2019/2211
(Continued)

(56) References Cited

U.S. PATENT DOCUMENTS 4,654,431 A  3/1987  De Boer
5,792,135 A  8/1998  Madhani et al.
(Continued)

OTHER PUBLICATIONS

U.S. Appl. No. 61/550,768, filed Oct. 24, 2011.
(Continued)

*Primary Examiner* — Allen Porter, Jr.
(74) *Attorney, Agent, or Firm* — Frost Brown Todd LLC

(57) ABSTRACT

A surgical device for operating on tissue comprises an end effector, a disposable shaft assembly, and an interface assembly. The shaft assembly comprises an articulation section operable to provide deflection of the end effector relative to the longitudinal axis of the shaft. The interface assembly comprises a plurality of pivotable base sections. The interface assembly comprises a plurality of drive components associated with drive shafts driven by an external system and each drive component is associated with a section of the base. The drive components are operable to cause rotation of one or both of the shaft or end effector and movement of components of the end effector. The drive components are further operable to cause articulation of the articulation section. The base sections are pivotable toward each other to couple with the shaft assembly or away from each other to disengage the shaft assembly.

19 Claims, 28 Drawing Sheets

(51) Int. Cl.
  *A61B 17/28* (2006.01)
  *A61B 17/29* (2006.01)
  *A61B 34/30* (2016.01)
  *A61B 17/00* (2006.01)

(52) U.S. Cl.
  CPC .......... *A61B 17/2816* (2013.01); *A61B 17/29* (2013.01); *A61B 34/30* (2016.02); *A61B 18/1445* (2013.01); *A61B 2017/0046* (2013.01); *A61B 2017/00477* (2013.01); *A61B 2017/2947* (2013.01); *A61B 2018/1455* (2013.01)

(58) Field of Classification Search
  USPC .................................................. 606/41, 130
  See application file for complete search history.

(56) References Cited

U.S. PATENT DOCUMENTS

| | | | |
|---|---|---|---|
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,455,208 B2 | 11/2008 | Wales et al. | |
| 7,506,790 B2 | 3/2009 | Shelton, IV et al. | |
| 7,524,320 B2 | 4/2009 | Tierney et al. | |
| 7,549,564 B2 | 6/2009 | Boudreaux | |
| 7,559,450 B2 | 7/2009 | Wales et al. | |
| 7,654,431 B2 | 2/2010 | Hueil et al. | |
| 7,691,098 B2 | 4/2010 | Wallace et al. | |
| 7,780,054 B2 | 8/2010 | Wales | |
| 7,784,662 B2 | 8/2010 | Wales et al. | |
| 7,798,386 B2 | 9/2010 | Schall et al. | |
| 7,806,891 B2 | 10/2010 | Nowlin et al. | |
| 7,824,401 B2 | 11/2010 | Manzo et al. | |
| 8,182,469 B2 | 5/2012 | Anderson et al. | |
| 8,461,744 B2 | 6/2013 | Wiener et al. | |
| 8,479,969 B2 | 7/2013 | Shelton, IV et al. | |
| 8,480,671 B2 | 7/2013 | Mueller | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,752,749 B2 | 6/2014 | Moore et al. | |
| 9,023,071 B2 | 5/2015 | Miller et al. | |
| 9,107,685 B2 | 8/2015 | Parihar et al. | |
| 9,125,662 B2 | 9/2015 | Shelton, IV | |
| 9,161,803 B2 | 10/2015 | Yates et al. | |
| 9,220,559 B2 | 12/2015 | Worrell et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087218 A1 | 4/2011 | Boudreaux et al. | |
| 2011/0112517 A1* | 5/2011 | Peine ..................... | A61B 17/29 606/1 |
| 2011/0295269 A1 | 12/2011 | Swensgard et al. | |
| 2012/0078243 A1 | 3/2012 | Worrell et al. | |
| 2012/0078247 A1 | 3/2012 | Worrell et al. | |
| 2012/0078248 A1 | 3/2012 | Worrell et al. | |
| 2012/0116379 A1 | 5/2012 | Yates et al. | |
| 2012/0138660 A1 | 6/2012 | Shelton, IV et al. | |
| 2012/0199630 A1 | 8/2012 | Shelton, IV et al. | |
| 2012/0199632 A1 | 8/2012 | Spivey et al. | |
| 2012/0203247 A1 | 8/2012 | Shelton, IV et al. | |
| 2013/0012957 A1 | 1/2013 | Shelton, IV et al. | |
| 2013/0023868 A1 | 1/2013 | Worrell et al. | |
| 2013/0030428 A1 | 1/2013 | Worrell et al. | |
| 2013/0267969 A1 | 10/2013 | Martin et al. | |

OTHER PUBLICATIONS

U.S. Appl. No. 61/597,603, filed Feb. 10, 2012.
International Search Report and Written Opinion dated May 28, 2014 for Application No. PCT/US2014/016416, 9 pgs.

* cited by examiner

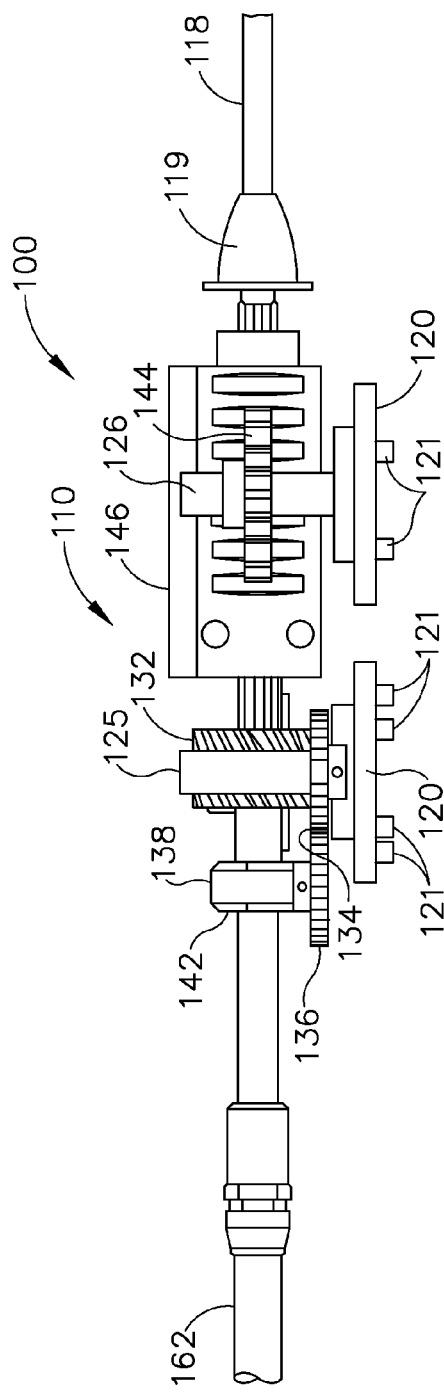
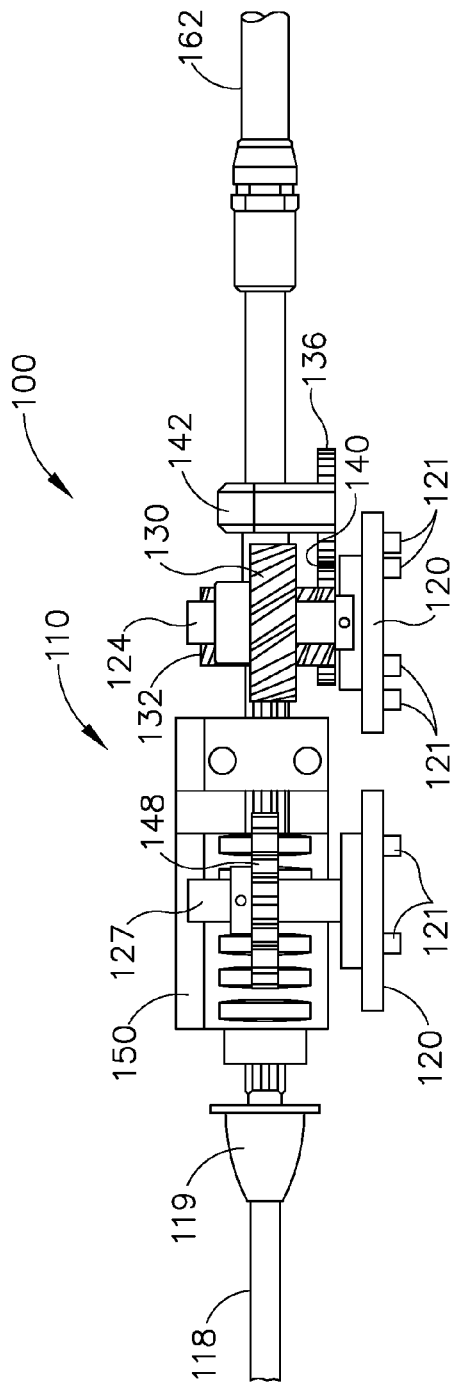
Fig. 12
Fig. 13

ELECTROSURGICAL DEVICE WITH DISPOSABLE SHAFT HAVING CLAMSHELL COUPLING

This application is a continuation of U.S. application Ser. No. 13/798,677, filed Mar. 13, 2013, published as U.S. Pub. No. 2014/0276776, now U.S. Pat. No. 9,107,685, issued on Aug. 18, 2015, entitled "Electrosurgical Device with Disposable Shaft Having Clamshell Coupling."

BACKGROUND

A variety of surgical instruments include a tissue cutting element and one or more elements that transmit radio frequency (RF) energy to tissue (e.g., to coagulate or seal the tissue). An example of an RF electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued on Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued on Jan. 17, 2017, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein; U.S. patent application Ser. No. 13/443,101, entitled "Control Interface for Laparoscopic Suturing Instrument," filed Apr. 10, 2012, published as U.S. Pub. No. 2013/0267969 on Oct. 3, 2013, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts a left side elevational view of the instrument of FIG. 4, with the top cover removed;

FIG. 13 depicts a right side elevational view of the instrument of FIG. 4, with the top cover removed;

Figure 1:
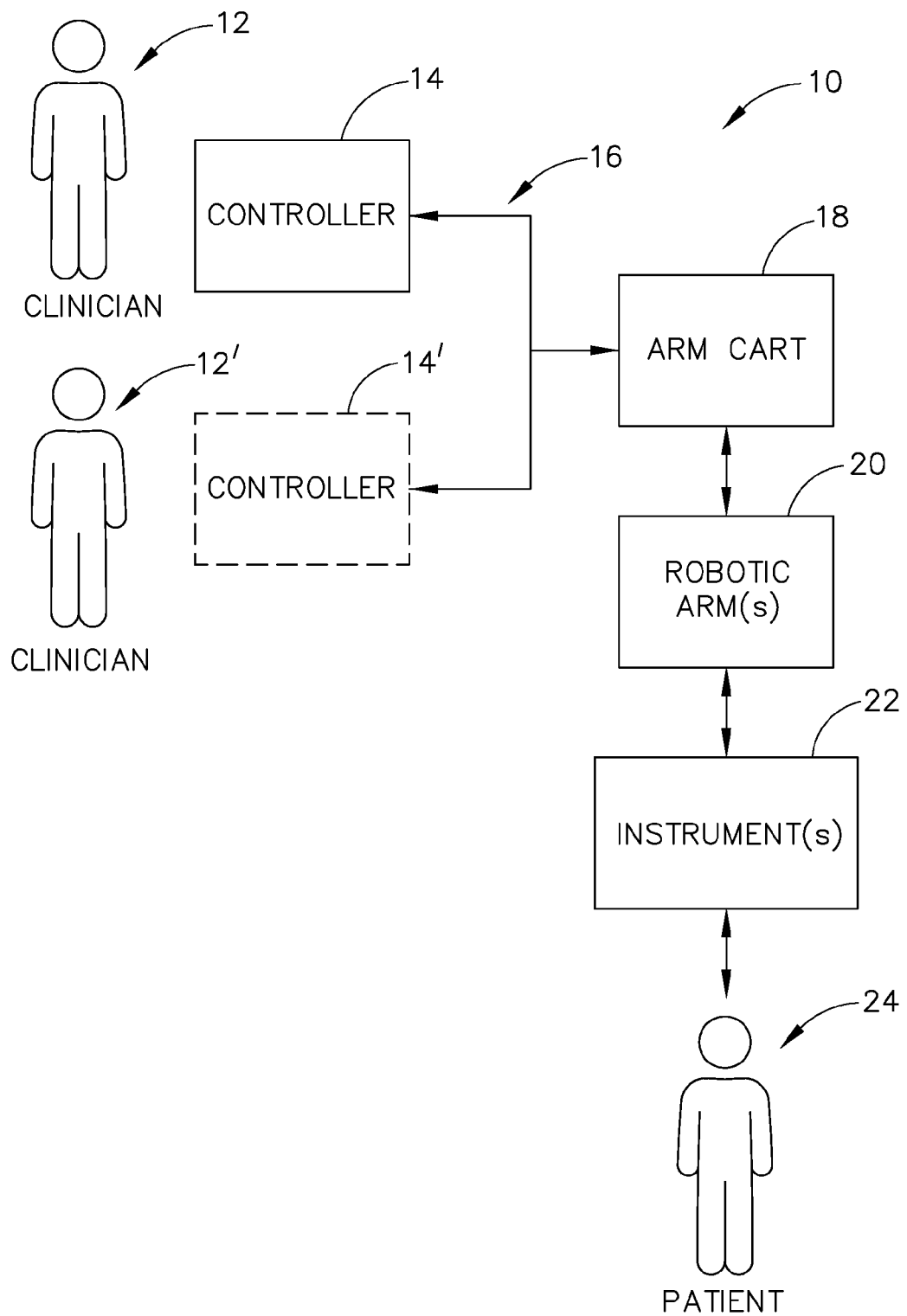
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
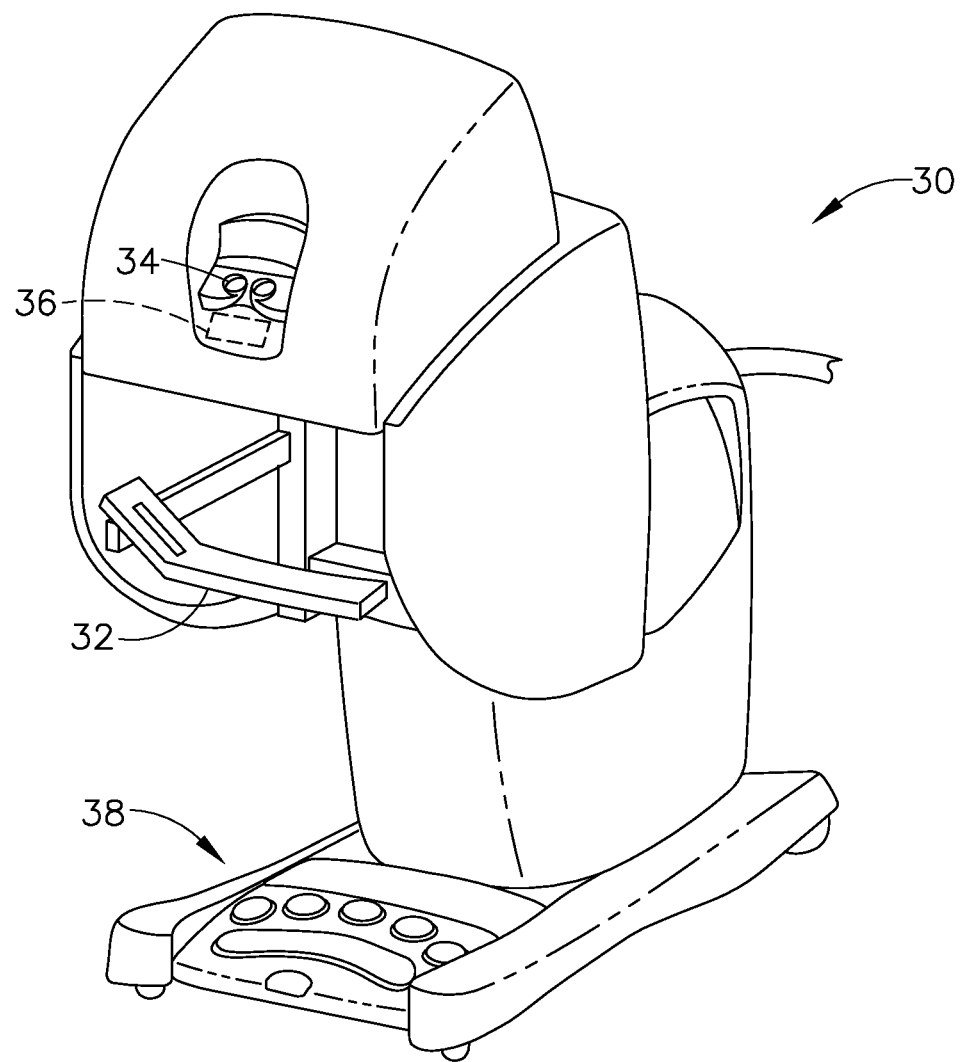
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge has been loaded into an end effector of instrument (22), whether an anvil of instrument (22) has been moved to a closed position prior to firing, and/or some other operational condition of instrument (22).

Figure 3:
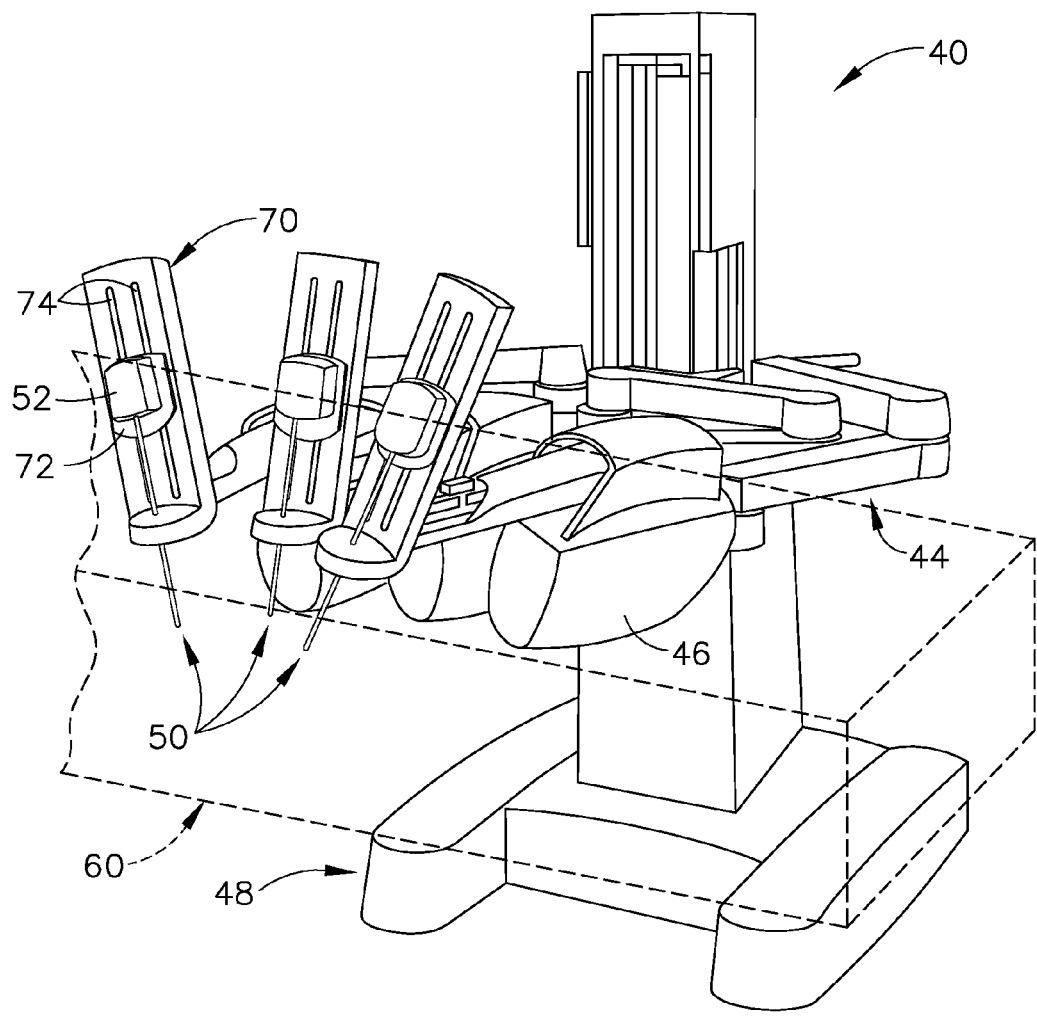
FIG. 3 depicts a perspective view of an exemplary robotic arm cart of the system of FIG. 1.
Figure 4:
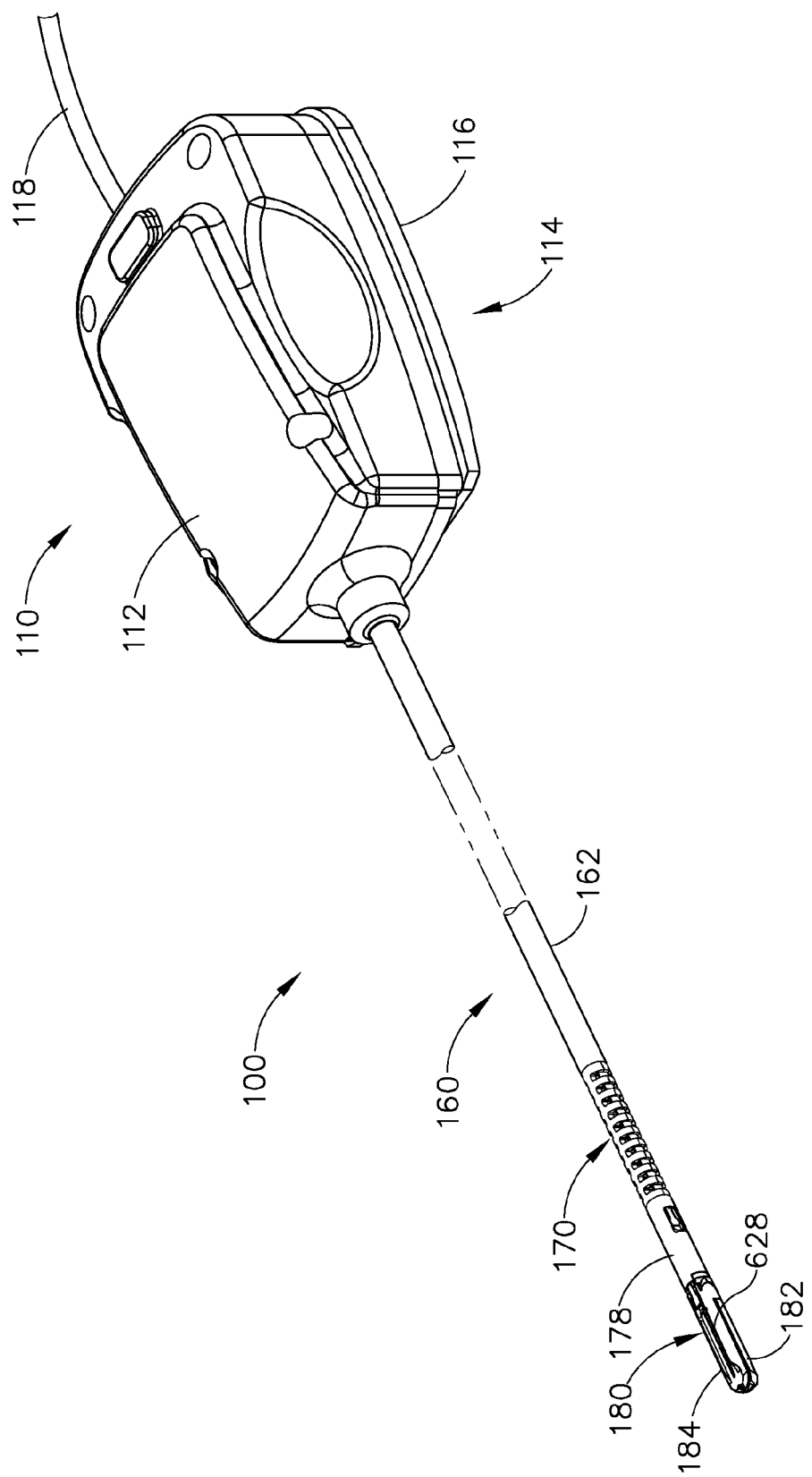
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. Nos. 5,792,135; 5,817,084; 5,878,193; 6,231,565; 6,783, 524; 6,364,888; 7,524,320; 7,691,098; 7,806,891; 7,824, 401; and/or U.S. Pub. No. 2013/0012957, issued as U.S. Pat. No. 8,844,789. The disclosures of each of the foregoing U.S. Patents and U.S. Patent Publication are incorporated by reference herein. Still other suitable features and operabilities that may be incorporated into system (10) will be apparent to those of ordinary skill in the art in view of the teachings herein.

II. Exemplary Electrosurgical Instrument with Articulation Feature

FIGS. 4-13 show an exemplary electrosurgical instrument (100) that may be used as at least one instrument (50) within system (10). At least part of instrument (100) may be constructed and operable in accordance with at least some of the teachings of U.S. Pat. Nos. 6,500,176; 7,112,201; 7,125, 409; 7,169,146; 7,186,253; 7,189,233; 7,220,951; 7,309, 849; 7,311,709; 7,354,440; 7,381,209; U.S. Pub. No. 2011/ 0087218, issued as U.S. Pat. No. 8,939,974; U.S. Pub. No. 2012/0116379, now U.S. Pat. No. 9,161,803, issued on Oct. 20, 2015; U.S. Pub. No. 2012/0078243; U.S. Pub. No. 2012/0078247, now U.S. Pat. No. 9,402,682, issued on Aug. 2, 2016; U.S. Pub. No. 2013/0030428, now U.S. Pat. No. 9,402,682, issued on Aug. 2, 2016; and/or U.S. Pub. No. 2013/0023868, now U.S. Pat. No. 9,545,253, issued on Jan. 17, 2017. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of bipolar RF energy instead of providing lines of staples to join tissue. It should also be understood that instrument (100) may have various structural and functional similarities with the ENSEAL® Tissue Sealing Device by Ethicon Endo-Surgery, Inc., of Cincinnati, Ohio. Furthermore, instrument (100) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to instrument (100), there is no intent for any of the description herein to be presumed as admitted prior art. Several teachings herein will in fact go beyond the scope of the teachings of the references cited herein and the ENSEAL® Tissue Sealing Device by Ethicon Endo-Surgery, Inc., of Cincinnati, Ohio.

Instrument (100) of the present example includes an interface assembly (110), a shaft assembly (160), an articulation section (170), and an end effector (180). Interface assembly (110) is configured to couple with a dock (72) of robotic arm cart (40) and is thereby further operable to drive articulation section (170) and end effector (180) as will be described in greater detail below. As will also be described in greater detail below, instrument (100) is operable to articulate end effector (180) to provide a desired positioning relative to tissue (e.g., a large blood vessel, etc.), then sever the tissue and apply bipolar RF energy to the tissue with end effector (180) to thereby seal the tissue.

A. Exemplary Shaft Assembly and Articulation Section

Figure 5:
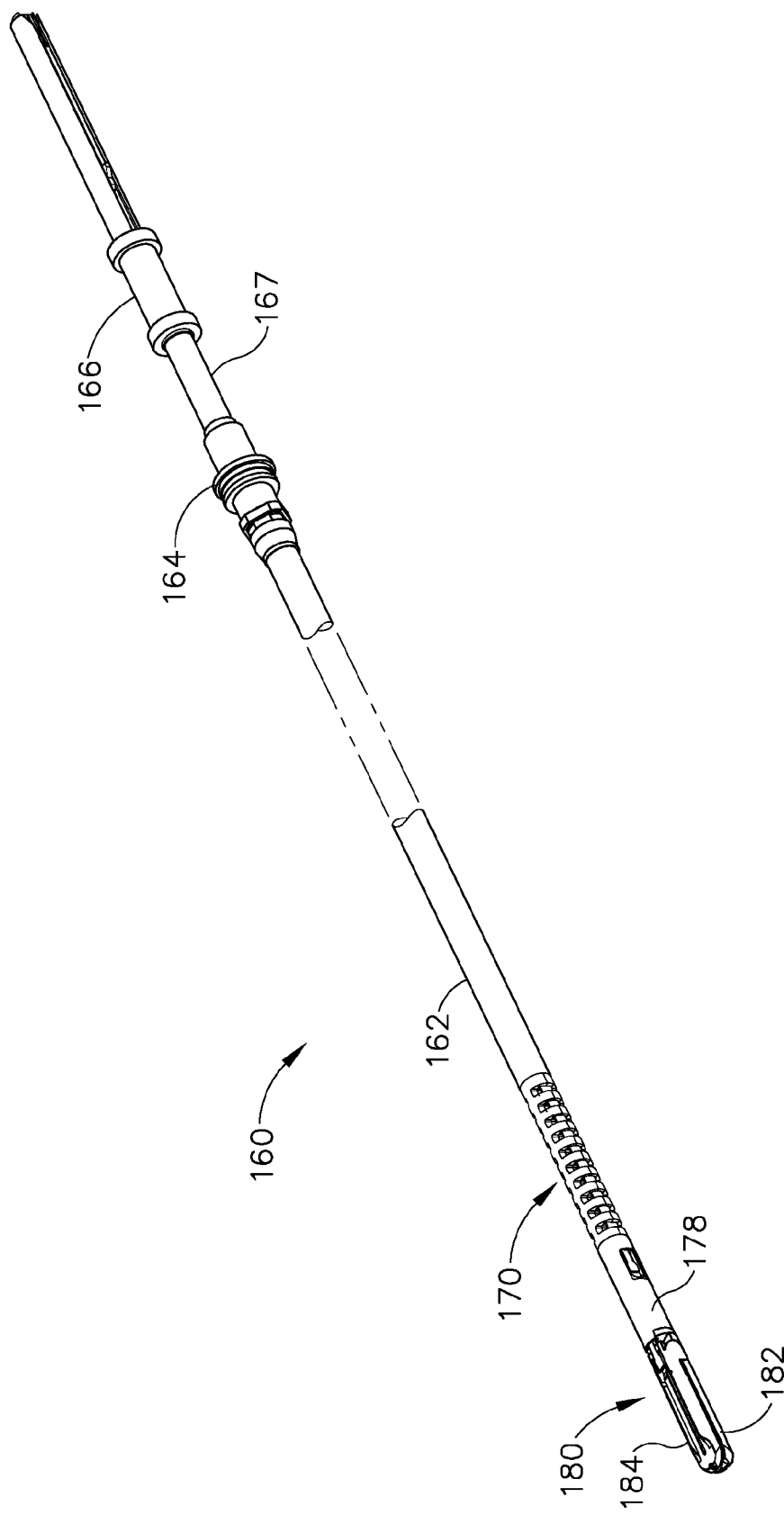
FIG. 5 depicts a perspective view of the shaft assembly of the surgical instrument of FIG. 4.

Shaft assembly (160) of the present example extends distally from interface assembly (110). Articulation section (170) is located at the distal end of shaft assembly (160), with end effector (180) being located distal to articulation section (170). Shaft assembly (160) includes an outer sheath (162) that encloses drive features and electrical features that couple interface assembly (110) with articulation section (170) and end effector (180). As best seen in FIG. 5, shaft assembly (160) further includes a unitary rotary coupling (164) and a firing beam coupling (166). Shaft assembly (160) is rotatable about the longitudinal axis defined by sheath (162), relative to interface assembly (110), via rotary coupling (164). Such rotation may provide rotation of end effector (180), articulation section (170), and shaft assembly (160) unitarily. In some other versions, rotary coupling (164) is operable to rotate end effector (180) without rotating any portion of shaft assembly (160) that is proximal of articulation section (170). As another merely illustrative example, instrument (100) may include one rotation control that provides rotatability of shaft assembly (160) and end effector (180) as a single unit; and another rotation control that provides rotatability of end effector (180) without rotating any portion of shaft assembly (160) that is proximal of articulation section (170). Other suitable rotation schemes will be apparent to those of ordinary skill in the art in view of the teachings herein. Of course, rotatable features may simply be omitted if desired.

Articulation section (170) is operable to selectively position end effector (180) at various angles relative to the longitudinal axis defined by sheath (162). Articulation section (170) may take a variety of forms. By way of example only, articulation section (170) may be configured in accordance with one or more teachings of U.S. Pub. No. 2012/0078247, now U.S. Pat. No. 9,402,682, issued on Aug. 2, 2016, the disclosure of which is incorporated by reference herein. As another merely illustrative example, articulation section (170) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued on Dec. 29, 2015, the disclosure of which is incorporated by reference herein. Various other suitable forms that articulation section (170) may take will be apparent to those of ordinary skill in the art in view of the teachings herein. It should also be understood that some versions of instrument (10) may simply lack articulation section (170).

Figure 6:
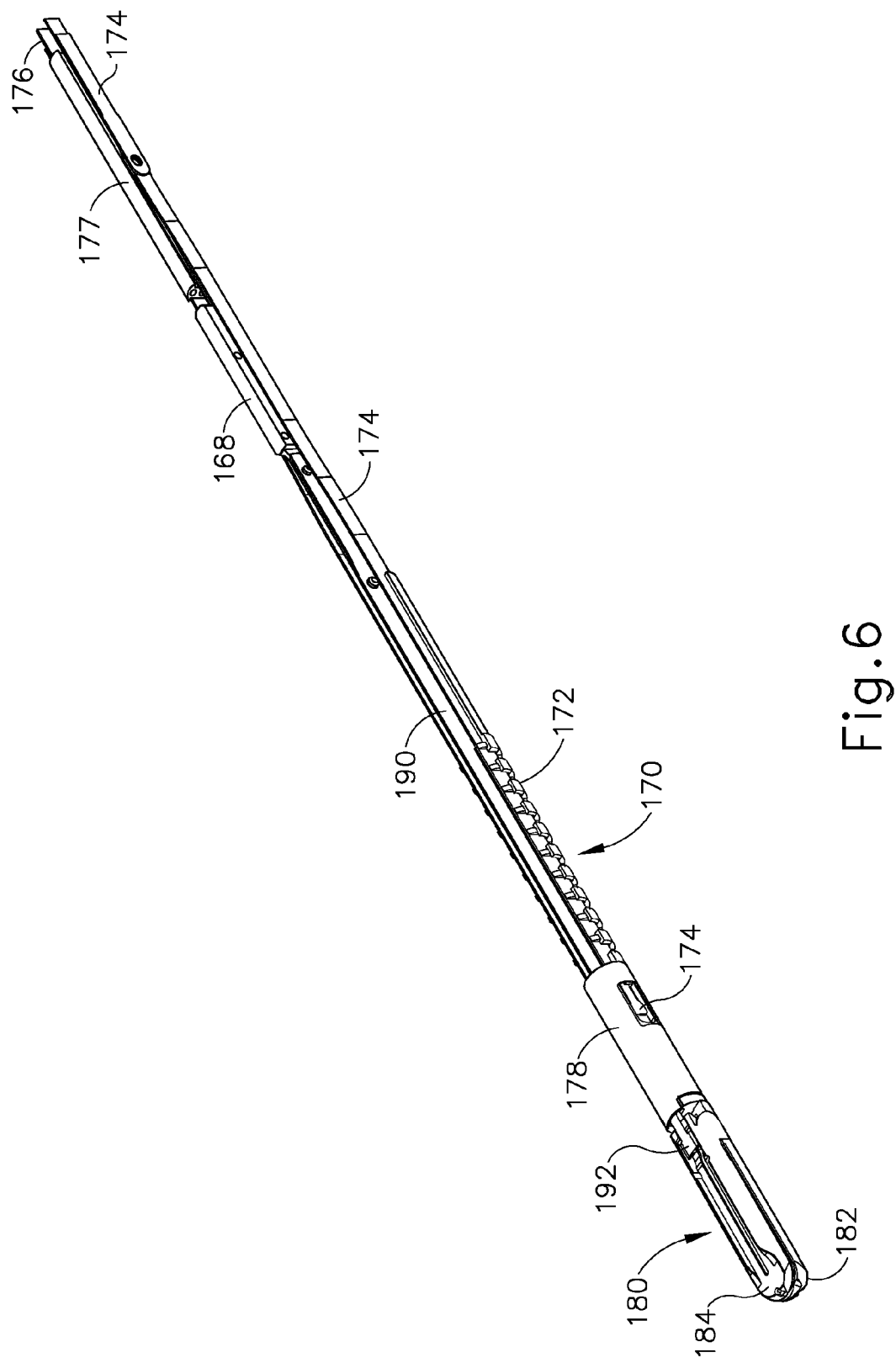
FIG. 6 depicts a perspective view of components of the shaft assembly of FIG. 5.
Figure 7:
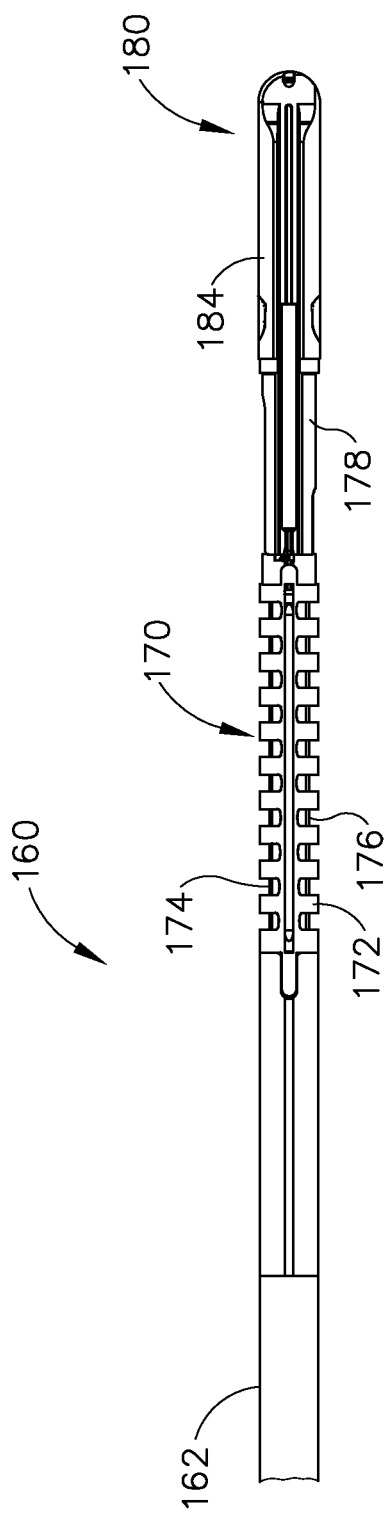
FIG. 7 depicts a top plan view of a distal portion of the shaft assembly of FIG. 5.

As best seen in FIGS. 6-7, articulation section (170) of the present example comprises a ribbed body (172) with a pair of articulation beams (174, 176) extending through ribbed body (172). An upper half of ribbed body (172) is omitted in FIG. 6. Articulation beams (174, 176) are distally anchored within a tube (178) that is positioned between end effector (180) and articulation section (170). Articulation beams (174, 176) are operable to articulate end effector (180) by laterally deflecting end effector (180) away from the longitudinal axis defined by sheath (162). In particular, and referring to the view shown in FIG. 7, end effector (180) will deflect toward articulation beam (174) when articulation beam (174) is retracted proximally while articulation beam (176) is advanced distally. End effector (180) will deflect toward articulation beam (176) when articulation beam (176) is retracted proximally while articulation beam (174) is advanced distally. Merely illustrative examples of how articulation beams (174, 176) may be opposingly translated will be described in greater detail below, while still other examples will be apparent to those of ordinary skill in the art in view of the teachings herein. As best seen in FIG. 6, a spacer body (177) is positioned between articulation beams (174, 176) and is operable to maintain beams (174, 176) in a substantially straight, separated relationship.

B. Exemplary End Effector

End effector (180) of the present example comprises a first jaw (182) and a second jaw (184). In the present example, first jaw (182) is substantially fixed relative to shaft assembly (160); while second jaw (184) pivots relative to shaft assembly (160), toward and away from first jaw (182). In some versions, actuators such as rods or cables, etc., may extend through sheath (162) and be joined with second jaw (184) at a pivotal coupling, such that longitudinal movement of the actuator rods/cables/etc. through shaft assembly (160) provides pivoting of second jaw (184) relative to shaft assembly (160) and relative to first jaw (182). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (190), such that actuator rods/cables/etc. may simply be eliminated in some versions.

Figure 8:
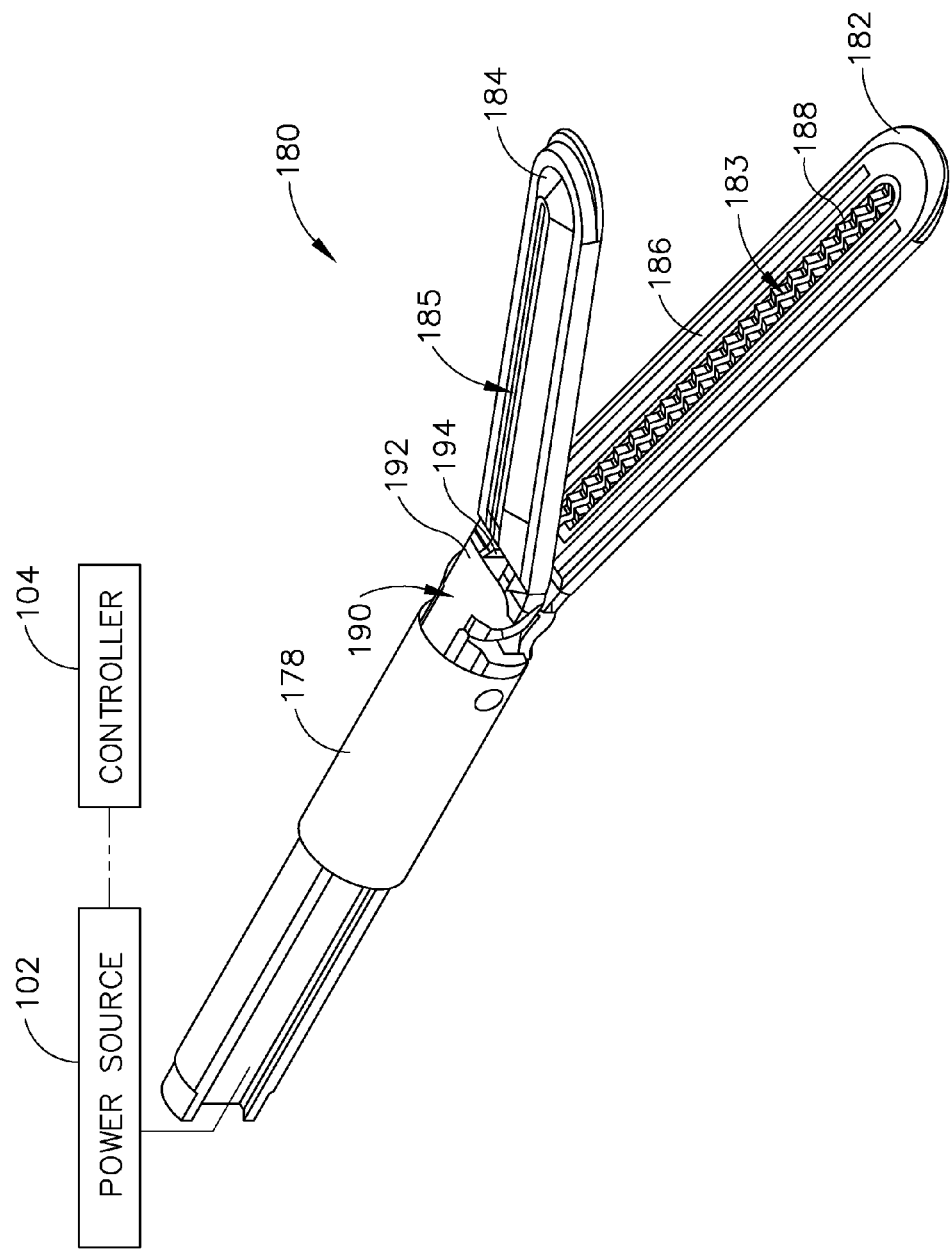
FIG. 8 depicts a perspective view of the end effector of the shaft assembly of FIG. 5, in an open configuration.
Figure 9:
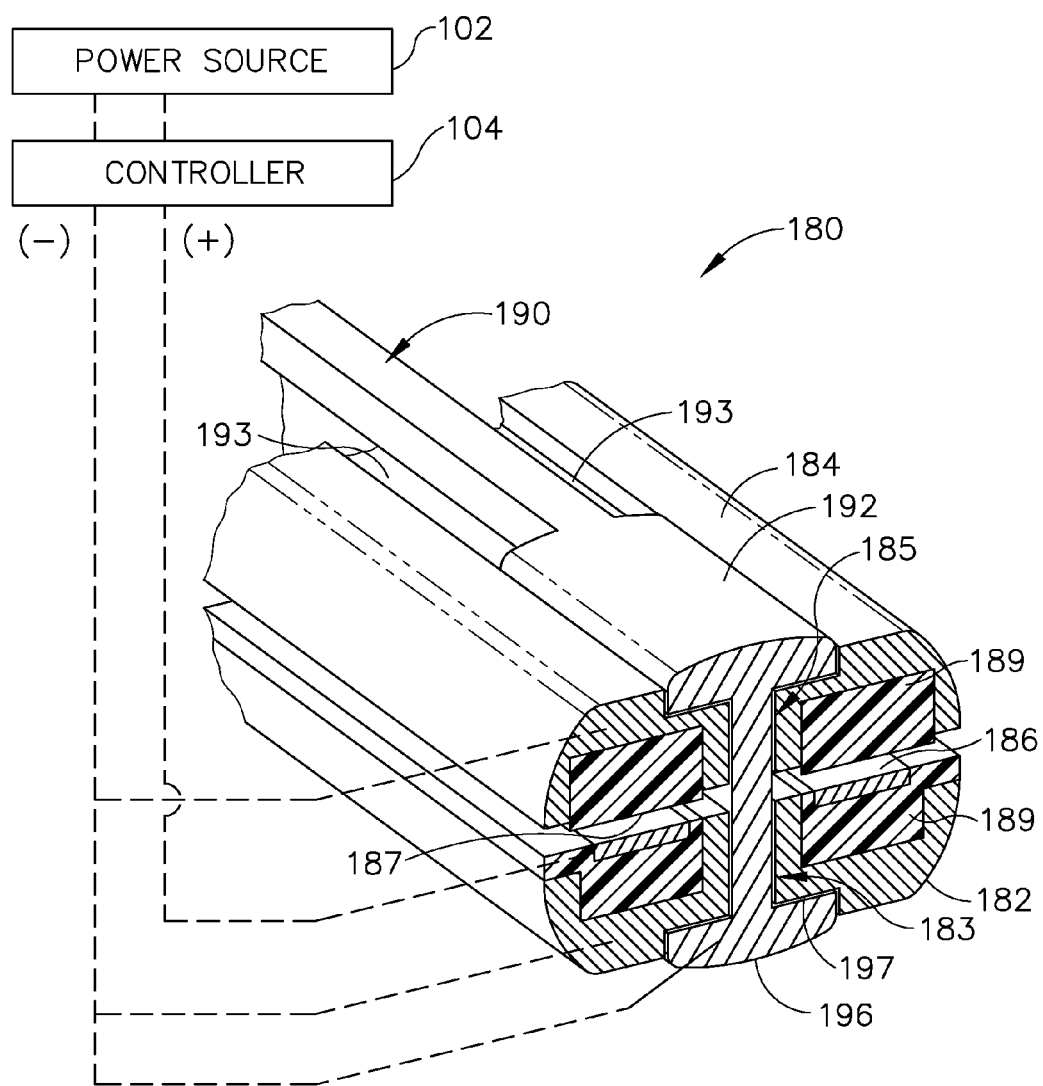
FIG. 9 depicts a perspective view in cross-section of the end effector of FIG. 8, taken along a lateral plane, with the end effector in a closed configuration.

As best seen in FIGS. 8-9, first jaw (182) defines a longitudinally extending elongate slot (183); while second jaw (184) also defines a longitudinally extending elongate slot (185). In addition, the top side of first jaw (182) presents a first electrode surface (186); while the underside of second jaw (184) presents a second electrode surface (187). Electrode surface (186, 187) are in communication with an electrical source (102) via one or more conductors (not shown) that extend along the length of shaft assembly (160). Electrical source (102) is operable to deliver RF energy to first electrode surface (186) at a first polarity and to second electrode surface (187) at a second (opposite) polarity, such that RF current flows between electrode surface (186, 187) and thereby through tissue captured between jaws (182, 184). In some versions, firing beam (190) serves as an electrical conductor that cooperates with electrode surface (186, 187) (e.g., as a ground return) for delivery of bipolar RF energy captured between jaws (182, 184).

Electrical source (102) may be external to instrument (100) or may be integral with instrument (100), as described in one or more references cited herein or otherwise. A controller (104) regulates delivery of power from electrical source (102) to electrode surfaces (186, 187). Controller (104) may also be external to instrument (100) or may be integral with electrosurgical instrument (100), as described in one or more references cited herein or otherwise. It should also be understood that electrode surfaces (186, 187) may be provided in a variety of alternative locations, configurations, and relationships. It should also be understood that power source (102) and/or controller (104) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, issued as U.S. Pat. No. 8,951,248 on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, issued as U.S. Pat. No. 9,039,695 on May 26, 2015, the disclosure of which is incorporated by reference herein; U.S. Pub. No. 2011/0087215, entitled "Surgical Generator for Ultrasonic and Electrosurgical Devices," published Apr. 14, 2011, issued as U.S. Pat. No. 9,050,093 on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, issued as U.S. Pat. No. 8,956,349 on Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued on Jun. 23, 2015, the disclosure of which is incorporated by reference herein. Other suitable configurations for power source (102) and controller (104) will be apparent to those of ordinary skill in the art in view of the teachings herein.

As best seen in FIG. 9, the lower side of first jaw (182) includes a longitudinally extending recess (197) adjacent to slot (183); while the upper side of second jaw (184) includes a longitudinally extending recess (193) adjacent to slot (185). FIG. 2 shows the upper side of first jaw (182) including a plurality of teeth serrations (188). It should be understood that the lower side of second jaw (184) may include complementary serrations that nest with serrations (188), to enhance gripping of tissue captured between jaws (182, 184) without necessarily tearing the tissue. Of course, serrations (188) may take any other suitable form or may be simply omitted altogether. It should also be understood that serrations (188) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (182, 184).

With jaws (182, 184) in a closed position, shaft assembly (160) and end effector (180) are sized and configured to fit through trocars having various inner diameters, such that instrument (100) is usable in minimally invasive surgery, though of course instrument (100) could also be used in open procedures if desired. By way of example only, with jaws (182, 184) in a closed position, shaft assembly (160) and end effector (180) may present an outer diameter of approximately 5 mm. Alternatively, shaft assembly (160) and end effector (180) may present any other suitable outer diameter (e.g., between approximately 2 mm and approximately 20 mm, etc.).

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (189) (e.g., PTC polymer, etc.), located adjacent to electrodes (186, 187) and/or elsewhere. Data from sensors may be communicated to controller (104). Controller (104) may process such data in a variety of ways. By way of example only, controller (104) may modulate or otherwise change the RF energy being delivered to electrode surface (186, 187), based at least in part on data acquired from one or more sensors at end effector (180). In addition or in the alternative, controller (104) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (104), and may simply provide a purely localized effect at end effector (180). For instance, PTC thermistor bodies (189) at end effector (180) may automatically reduce the energy delivery at electrode surface (186, 187) as the temperature of the tissue and/or end effector (180) increases, thereby reducing the likelihood of overheating. In some such versions, a PTC thermistor element is in series with power source (102) and electrode surface (186, 187); and the PTC thermistor provides an increased impedance (reducing flow of current) in response to temperatures exceeding a threshold. Furthermore, it should be understood that electrode surface (186, 187) may be used as sensors (e.g., to sense tissue impedance, etc.). Various kinds of sensors that may be incorporated into instrument (100) will be apparent to those of ordinary skill in the art in view of the teachings herein. Similarly various things that can be done with data from sensors, by controller (104) or otherwise, will be apparent to those of ordinary skill in the art in view of the teachings herein. Other suitable variations for end effector (180) will also be apparent to those of ordinary skill in the art in view of the teachings herein.

Firing beam (190) is longitudinally movable along part of the length of end effector (180). Firing beam (190) is coaxially positioned within shaft assembly (160), extends along part of the length of shaft assembly (160), and translates longitudinally within shaft assembly (160) (including articulation section (170) in the present example), though it should be understood that firing beam (190) and shaft assembly (160) may have any other suitable relationship. As shown in FIG. 6, firing beam (190) is secured to a firing block (168), such that firing beam (190) and firing block (168) translate unitarily together within sheath (162). Firing block (168) is secured to firing tube (167), which is best seen in FIG. 5. Firing block (168) and firing tube (167) translate unitarily together within sheath (162). Firing beam coupling (166) is secured to firing tube (167), such that translating firing beam coupling (166) will translate firing beam (190) through the above-described couplings.

Firing beam (190) includes a sharp distal blade (194), an upper flange (192), and a lower flange (196). As best seen in FIGS. 8-9, distal blade (194) extends through slots (183, 185) of jaws (182, 184), with upper flange (192) being located above jaw (184) in recess (59) and lower flange (196) being located below jaw (182) in recess (58). The configuration of distal blade (194) and flanges (62, 66) provides an "I-beam" type of cross section at the distal end of firing beam (190). While flanges (192, 196) extend longitudinally only along a small portion of the length of firing beam (190) in the present example, it should be understood that flanges (192, 196) may extend longitudinally along any suitable length of firing beam (190). In addition, while flanges (192, 196) are positioned along the exterior of jaws (182, 184), flanges (192, 196) may alternatively be disposed in corresponding slots formed within jaws (182, 184). For instance, each jaw (182, 184) may define a "T"-shaped slot, with parts of distal blade (194) being disposed in one vertical portion of each "T"-shaped slot and with flanges (192, 196) being disposed in the horizontal portions of the "T"-shaped slots. Various other suitable configurations and relationships will be apparent to those of ordinary skill in the art in view of the teachings herein.

Distal blade (194) is substantially sharp, such that distal blade (194) will readily sever tissue that is captured between jaws (182, 184). Distal blade (194) is also electrically grounded in the present example, providing a return path for RF energy as described elsewhere herein. In some other versions, distal blade (194) serves as an active electrode. In addition or in the alternative, distal blade (194) may be selectively energized with ultrasonic energy (e.g., harmonic vibrations at approximately 55.5 kHz, etc.).

The "I-beam" type of configuration of firing beam (190) provides closure of jaws (182, 184) as firing beam (190) is advanced distally. In particular, flange (192) urges jaw (184) pivotally toward jaw (182) as firing beam (190) is advanced from a proximal position to a distal position, by bearing against recess (193) formed in jaw (184). This closing effect on jaws (182, 184) by firing beam (190) may occur before distal blade (194) reaches tissue captured between jaws (182, 184). Such staging of encounters by firing beam (190) may reduce the force required to actuate firing beam (190) distally through a full firing stroke. In other words, in some such versions, firing beam (190) may have already overcome an initial resistance required to substantially close jaws (182, 184) on tissue before encountering resistance from severing the tissue captured between jaws (182, 184). Of course, any other suitable staging may be provided.

In the present example, flange (192) is configured to cam against a ramp feature at the proximal end of jaw (184) to open jaw (184) when firing beam (190) is retracted to a proximal position and to hold jaw (184) open when firing beam (190) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (190) is translated in the present example, it should be understood that other versions may provide independent movement of jaws (182, 184) and firing beam (190). By way of example only, one or more cables, rods, beams, or other features may extend through shaft assembly (160) to selectively actuate jaws (182, 184) independently of firing beam (190).

C. Exemplary Robotic Arm Interface Assembly

FIGS. 4 and 10-13 show interface assembly (110) of the present example in greater detail. As shown, interface assembly (110) comprises a housing (112), a base (114), and a cable (118). Housing (112) comprises a shell that simply encloses drive components. In some versions, housing (112) also includes an electronic circuit board, chip, and/or other feature that is configured to identify instrument (100). Such identification may be carried out through cable (118). Cable (118) is configured to couple with power source (102) and controller (104). A strain relief (119) is provided at the interface of cable (118) and housing (112). It should be noted that housing (112) is omitted from FIGS. 11-13 for the sake of clarity.

Figure 10:
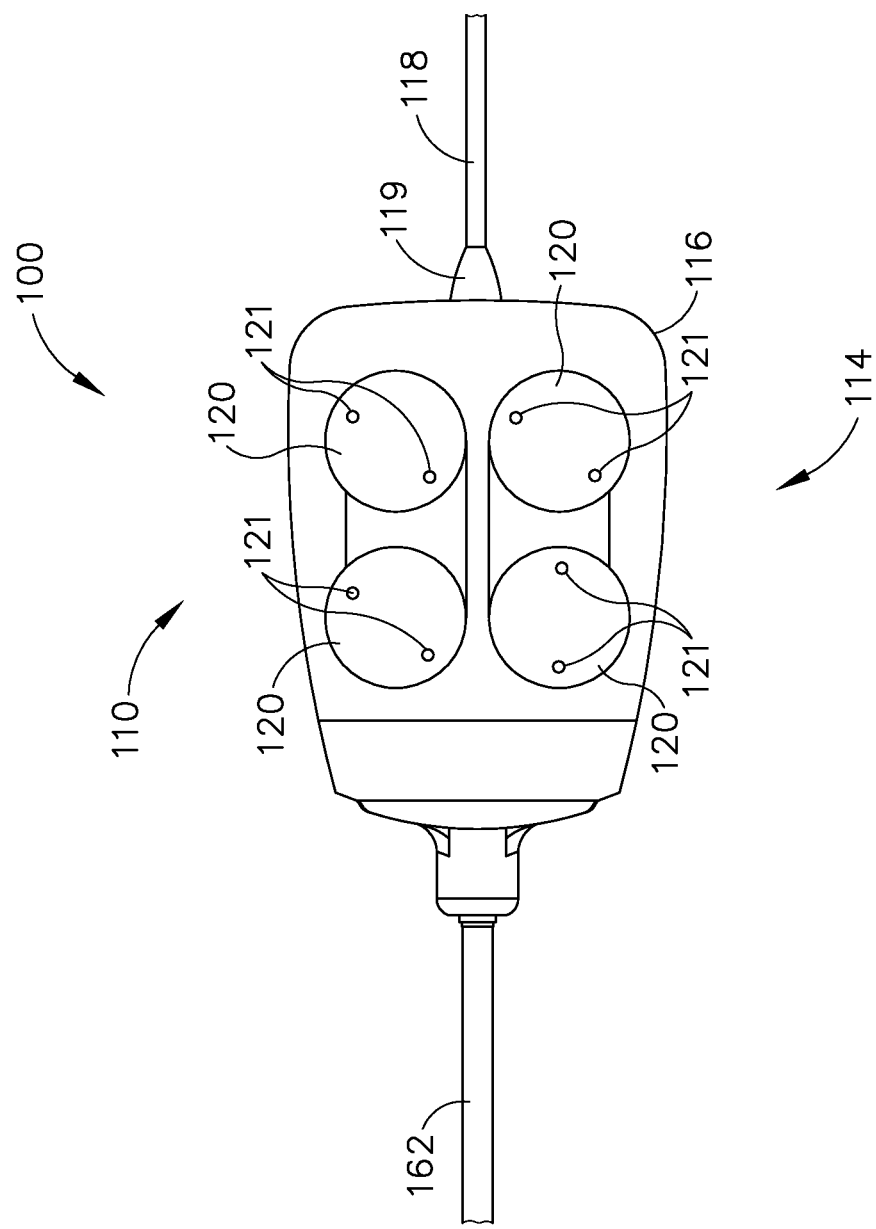
FIG. 10 depicts a bottom plan view of a proximal portion of the instrument of FIG. 4.
Figure 11:
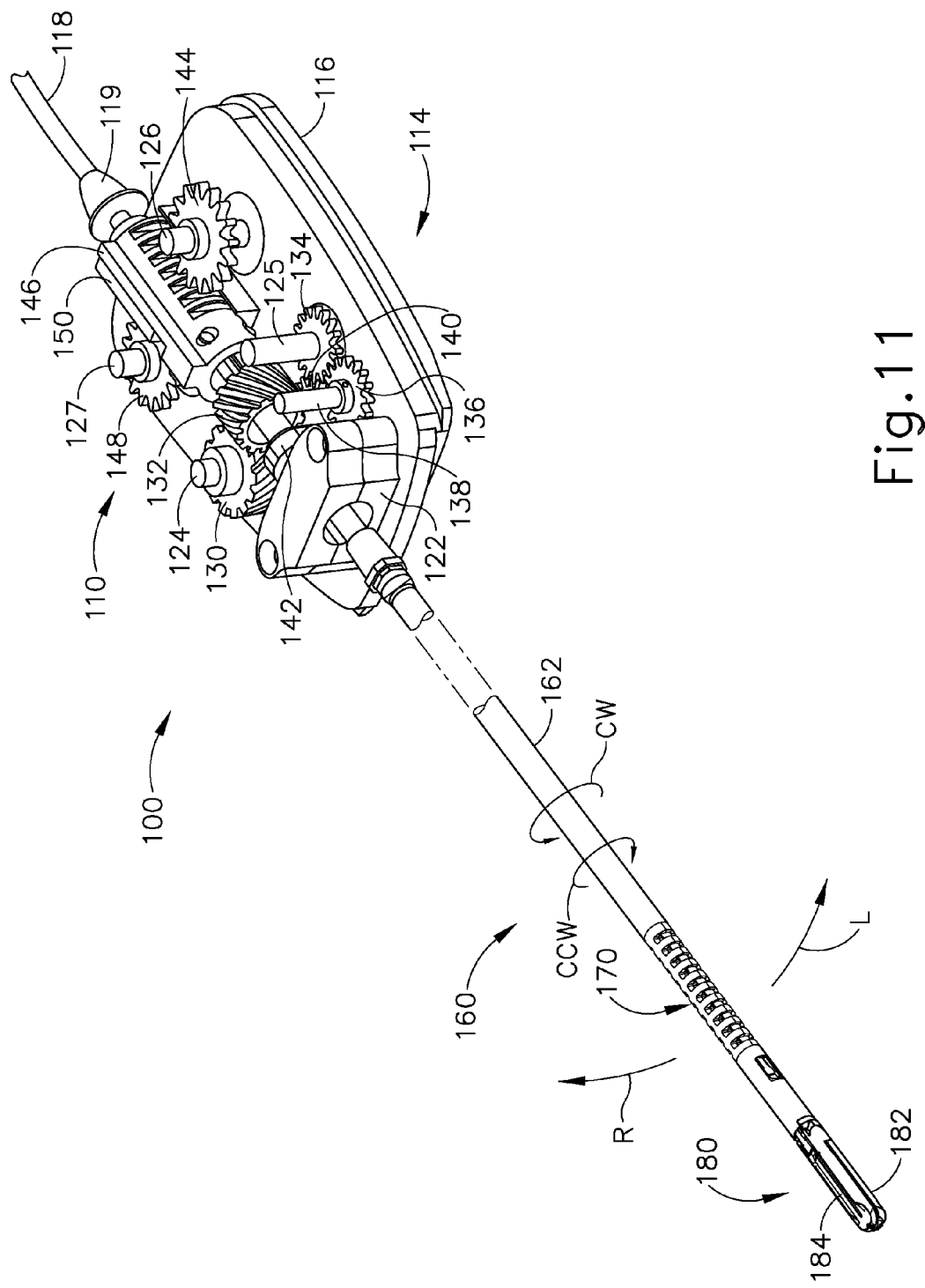
FIG. 11 depicts a perspective view of the instrument of FIG. 4, with a top cover removed.

Base (114) includes a mounting plate (116) that engages dock (72) of robotic arm cart (40). It should be noted that plate (116) is omitted from FIGS. 12-13 for the sake of clarity. While not shown, it should be understood that base (114) may also include one or more electrical contacts and/or other features operable to establish electrical communication with a complementary feature of dock (72). A shaft support structure (122) extends upwardly from base (114) and provides support to shaft assembly (160) (while still allowing shaft assembly (160) to rotate). By way of example only, shaft support structure (122) may include a busing, bearings, and/or other features that facilitate rotation of shaft assembly (160) relative to support structure (122). As shown in FIG. 10, base (114) further includes four drive discs (120) that are rotatable relative to plate (116). Each disc (120) includes a pair of unitary pins (121) that couple with complementary recesses (not shown) in drive elements of dock (72). In some versions, one pin (121) of each pair is closer to the axis of rotation of the corresponding disc (120), to ensure proper angular orientation of disc (120) relative to the corresponding drive element of dock (72). As best seen in FIGS. 11-13, a drive shaft (124, 125, 126, 127) extends unitarily upwardly from each disc (120). As will be described in greater detail below, discs (120) are operable to provide independent rotation of shaft assembly (160), bending of articulation section (170), and translation of firing beam (190), through rotation of drive shafts (124, 125, 126, 127).

As best seen in FIG. 11, a first helical gear (130) is fixedly secured to drive shaft (124), such that rotation of the corresponding disc (120) provides rotation of first helical gear (130). First helical gear (130) meshes with a second helical gear (132), which is fixedly secured to rotary coupling (164). Thus, rotation of first helical gear (130) provides rotation of shaft assembly (160). It should be understood that rotation of first helical gear (130) about a first axis is converted into rotation of second helical gear (132) about a second axis, which is orthogonal to the first axis. A clockwise (CW) rotation of second helical gear (132) results in CW rotation of shaft assembly (160). A counter-clockwise (CCW) rotation of second helical gear (132) results in CCW rotation of shaft assembly (160). Other suitable ways in which shaft assembly (160) may be rotated will be apparent to those of ordinary skill in the art in view of the teachings herein.

As best seen in FIGS. 11-12, a spur gear (134) is fixedly secured to drive shaft (125), such that rotation of the corresponding disc (120) provides rotation of spur gear (134). Spur gear (134) meshes with a first spur pinion (136), which is fixedly secured to a pinion shaft (138). Pinion shaft (138) is supported by base (116) and rotates freely relative to base (116), such that first spur pinion (136) is rotatable as an idler. It should therefore be understood that first spur pinion (136) rotates in response to rotation of spur gear (134). First spur pinion (136) also meshes with a rack (140), which is fixedly secured to a drive block (142). Drive block (142) is secured to firing beam coupling (166). Thus, rotation of first spur pinion (136) is converted to translation of firing beam (190) via rack (140), drive block (142), and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (125) via its corresponding disc (120). When this rotation is reversed, firing beam (190) retracts proximally, ultimately opening jaws (182, 184) to release tissue. Other suitable ways in which firing beam (190) may be translated will be apparent to those of ordinary skill in the art in view of the teachings herein.

With respect to articulation control, FIGS. 11-12 show a second spur pinion (144) fixedly secured to drive shaft (126), such that rotation of the corresponding disc (120) provides rotation of second spur pinion (144). Second spur pinion (144) meshes with a left rack (146), which is fixedly secured to articulation beam (174). It should be understood that articulation beam (174) will translate distally or proximally in response to rotation of drive shaft (126). Similarly, FIGS. 11 and 13 show a third spur pinion (148) fixedly secured to drive shaft (127), such that rotation of the corresponding disc (120) provides rotation of third spur pinion (148). Third spur pinion (148) meshes with a right rack (150), which is fixedly secured to articulation beam (176). It should be understood that articulation beam (176) will translate distally or proximally in response to rotation of drive shaft (127).

It should also be understood that drive shafts (126, 127) may be rotated in the same direction simultaneously in order to provide opposing translation of beams (174, 176). For instance, drive shaft (126) may be rotated clockwise to retract beam (174) proximally, with drive shaft (127) being rotated clockwise to advance beam (176) distally, to thereby deflect end effector (180) to the left (L) at articulation section (170). Conversely, drive shaft (126) may be rotated counter-clockwise to advance beam (174) distally, with drive shaft (127) being rotated counter-clockwise to retract beam (176) proximally, to deflect end effector (180) to the left (R) at articulation section (170). Other suitable ways in which end effector (180) may be articulated at articulation section (170) will be apparent to those of ordinary skill in the art in view of the teachings herein. By way of example only, articulation control may be provided in accordance with at least some of the teachings of U.S. Pub. No. 2012/0078243, the disclosure of which is incorporated by reference herein; and/or U.S. Pub. No. 2013/0023868, now U.S. Pat. No. 9,545,253, issued on Jan. 17, 2017, the disclosure of which is incorporated by reference herein. It should also be understood that some versions of instrument (100) may simply lack an articulation section (170) and corresponding control.

D. Exemplary Operation

In an exemplary use, arm cart (40) is used to insert end effector (180) into a patient via a trocar. Articulation section (170) is substantially straight when end effector (180) and part of shaft assembly (160) are inserted through the trocar. Drive shaft (124) may be rotated through drive features in dock (72) that are coupled with the corresponding disc (120), to position end effector (180) at a desired angular orientation relative to the tissue. Drive shafts (126, 126) may then be rotated through drive features in dock (72) that are coupled with the corresponding discs (120), to pivot or flex articulation section (170) of shaft assembly (160) in order to position end effector (180) at a desired position and orientation relative to an anatomical structure within the patient. Two layers of tissue of the anatomical structure are then captured between jaws (182, 184) by rotating drive shaft (125) to advance firing beam (190) distally through a first range of motion. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of instrument (100) is perpendicular to the longitudinal axis defined by end effector (180), etc.). In other words, the lengths of jaws (182, 184) may be oriented perpendicular to (or at least generally transverse to) the length of the blood vessel. As noted above, flanges (192, 196) cammingly act to pivot jaw (182) toward jaw (184) when firing beam (190) is actuated distally by rotating drive shaft (125).

With tissue layers captured between jaws (182, 184) firing beam (190) continues to advance distally in response to continued rotation of drive shaft (125). As firing beam (190) continues to advance distally, distal blade (194) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (192, 196) immediately above and below jaws (182, 184), respectively, may help keep jaws (182, 184) in a closed and tightly clamping position. In particular, flanges (192, 196) may help maintain a significantly compressive force between jaws (182, 184). With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). In some versions, electrodes (186, 187) are selectively coupled with power source (102) such that electrode surface (186, 187) of jaws (182, 184) are activated with a common first polarity while firing beam (190) is activated at a second polarity that is opposite to the first polarity. Thus, a bipolar RF current flows between firing beam (190) and electrode surfaces (186, 187) of jaws (182, 184), through the compressed regions of severed tissue layer portions. In some other versions, electrode surface (186) has one polarity while electrode surface (187) and firing beam (190) both have the other polarity. In either version (among at least some others), bipolar RF energy delivered by power source (102) ultimately thermally welds the tissue layer portions on one side of firing beam (190) together and the tissue layer portions on the other side of firing beam (190) together.

In certain circumstances, the heat generated by activated electrode surfaces (186, 187) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surface (186, 187) may be activated with bipolar RF energy before firing beam (190) even begins to translate distally and thus before the tissue is even severed. Other suitable ways in which instrument (100) may be operable and operated will be apparent to those of ordinary skill in the art in view of the teachings herein.

Figure 14:
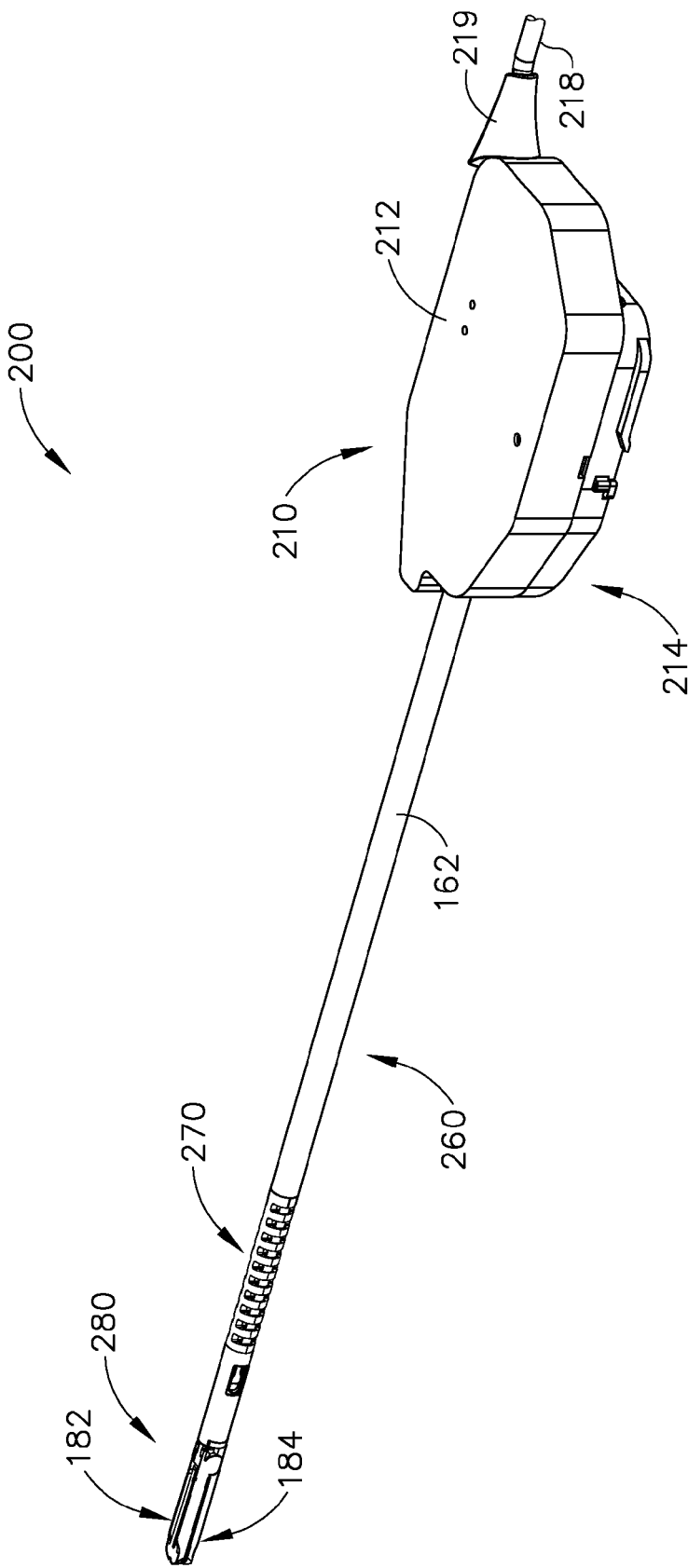
FIG. 14 depicts a perspective view of an exemplary alternative surgical instrument suitable for incorporation with the system of FIG. 1.

III. Exemplary Alternative Electrosurgical Instrument with Reusable Interface Assembly FIG. 14 shows an exemplary alternative electrosurgical instrument (200). Instrument (200) of this example is substantially similar to instrument (100) described above in that instrument (200) has an articulation section (270) and an end effector (280) that are substantially identical to articulation section (170) and end effector (180) described above. Instrument (200) of this example is also operable to couple with a dock (72) of robotic arm cart (40) via an interface assembly (210). However, as will be described in greater detail below, interface assembly (210) of this example is different from interface assembly (110) described above. Instrument (200) of this example also comprises a shaft assembly (260) which is substantially similar to shaft assembly (160) described above. However, shaft assembly (260) of this example is different from shaft assembly (160) described above—primarily in how shaft assembly (260) associates with interface assembly (210) compared to the association of shaft assembly (160) and interface assembly (110) described above.

FIGS. 15-18 show interface assembly (210) of the present example in greater detail. Interface assembly (210) comprises a housing (212), a pivoting base (214), and a cable (218). Housing (212) comprises a shell that simply encloses drive components. In some versions, housing (212) also includes an electronic circuit board, chip, and/or other feature that is configured to identify instrument (200). Such identification may be carried out through cable (218). Cable (218) is configured to couple with a power source (not shown) and a controller (not shown). A strain relief (219) is provided at the interface of cable (218) and housing (212). It should be noted that housing (212) is omitted from FIGS. 16-18, 23-24, and 28-29 for the sake of clarity. It should also be noted that cable (218) and strain relief (219) are merely optional. By way of example only, some versions of interface assembly (210) may include an integral power source (e.g., a battery, etc.).

Figure 15:
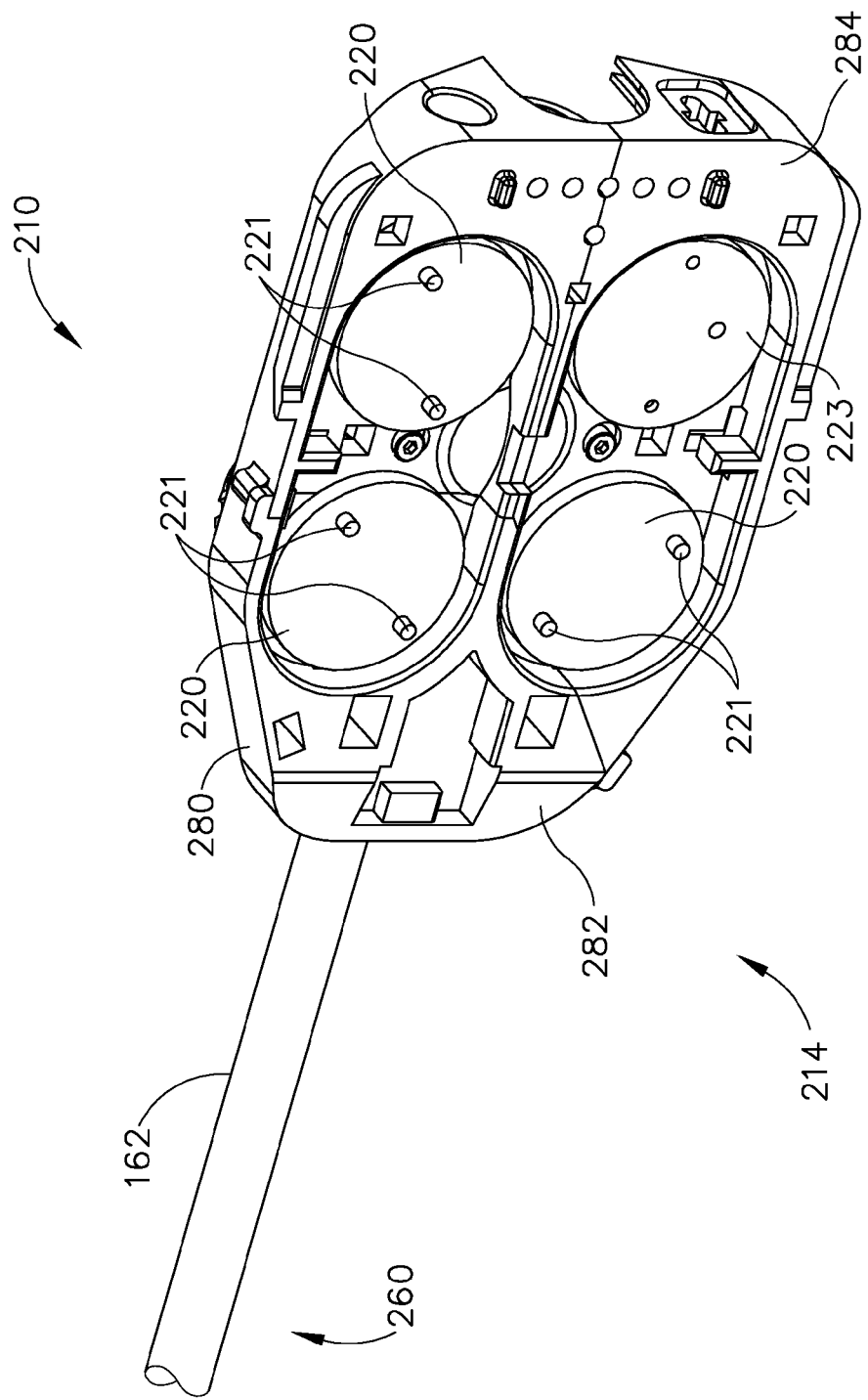
FIG. 15 depicts a bottom perspective view of the proximal portion of the surgical instrument of FIG. 14.
Figure 16:
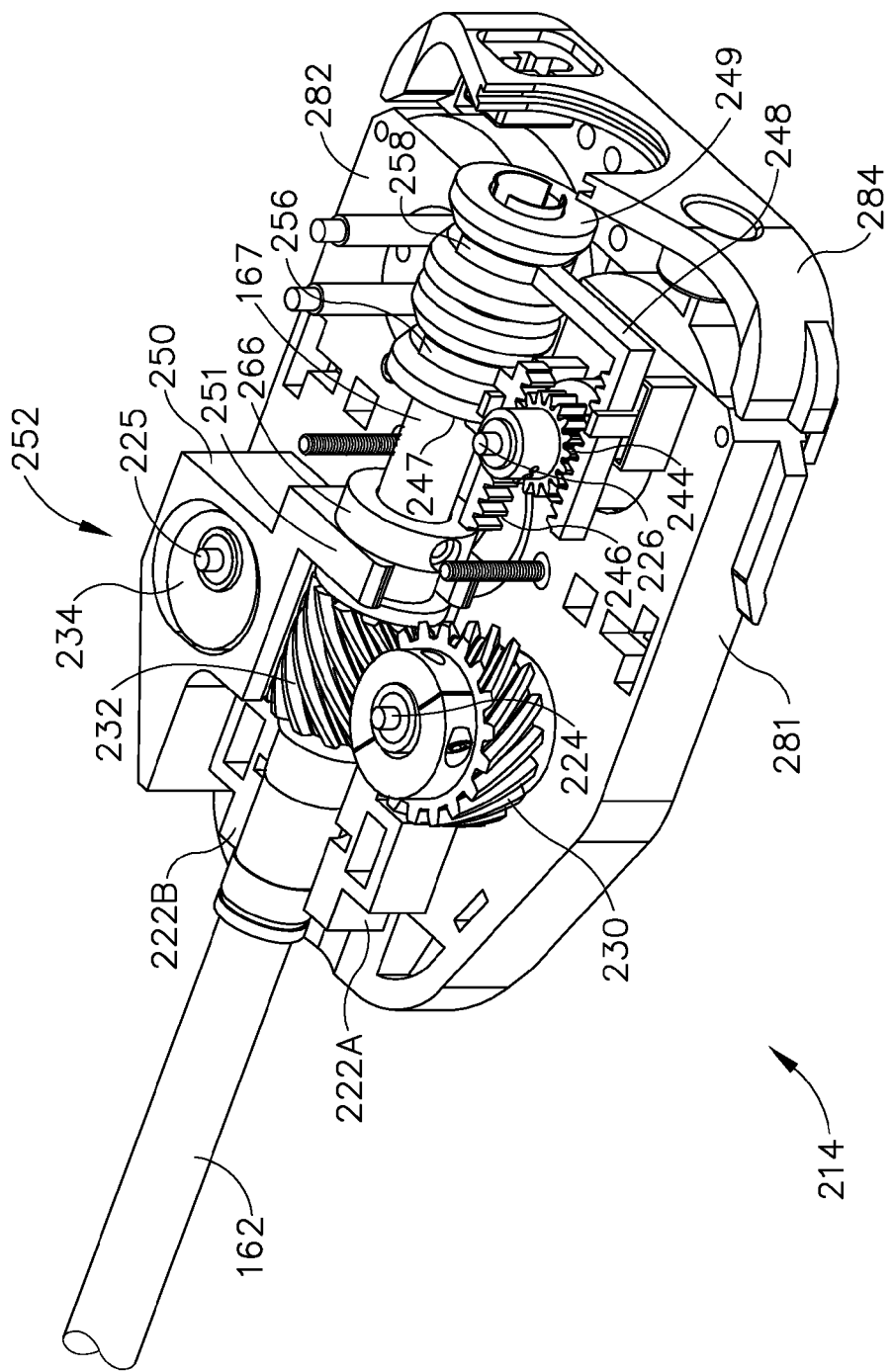
FIG. 16 depicts a top perspective view of the proximal portion of the surgical instrument of FIG. 14, with a top cover removed.
Figure 17:
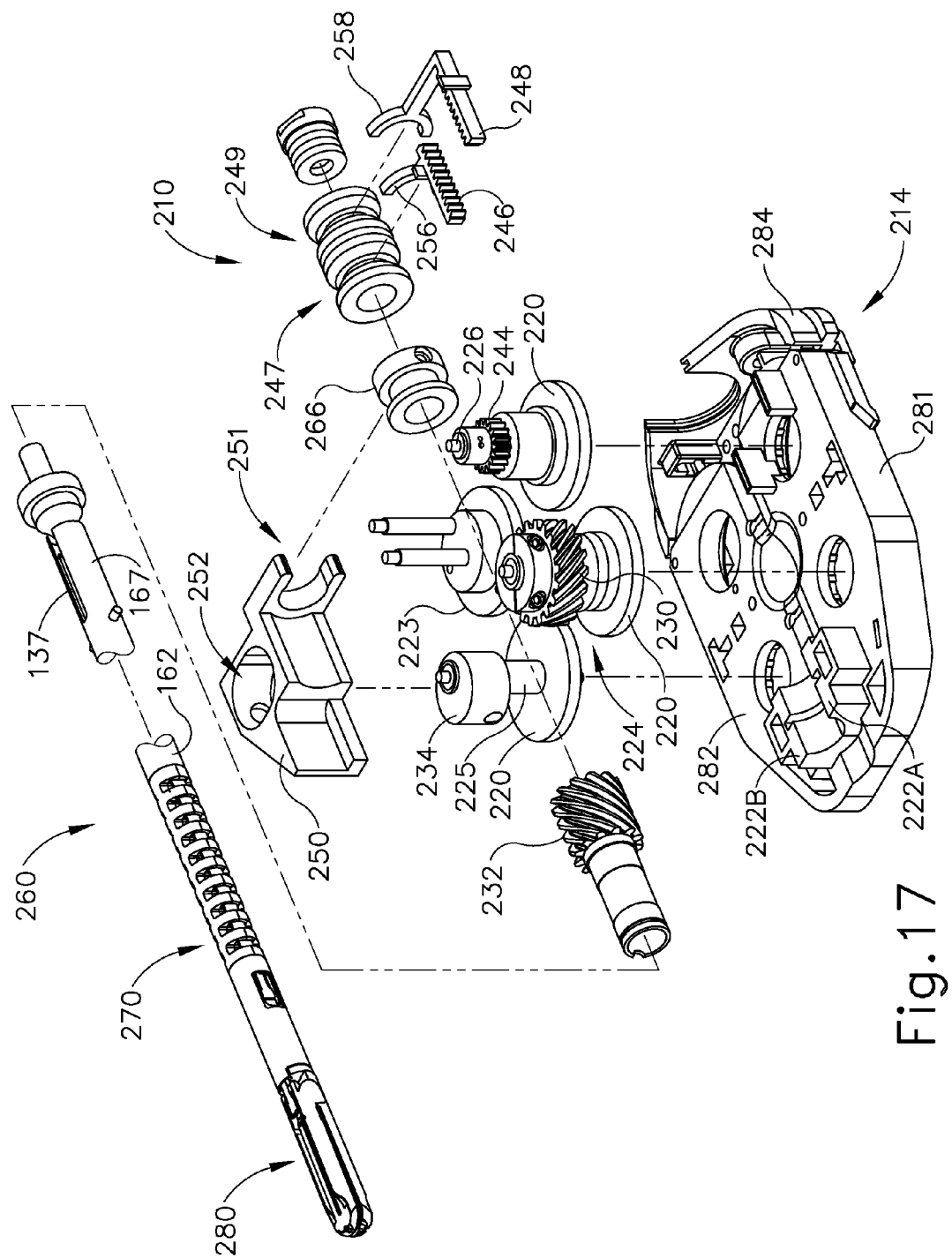
FIG. 17 depicts an exploded perspective view of the proximal portion of the surgical instrument of FIG. 14, with the top cover removed.
Figure 18:
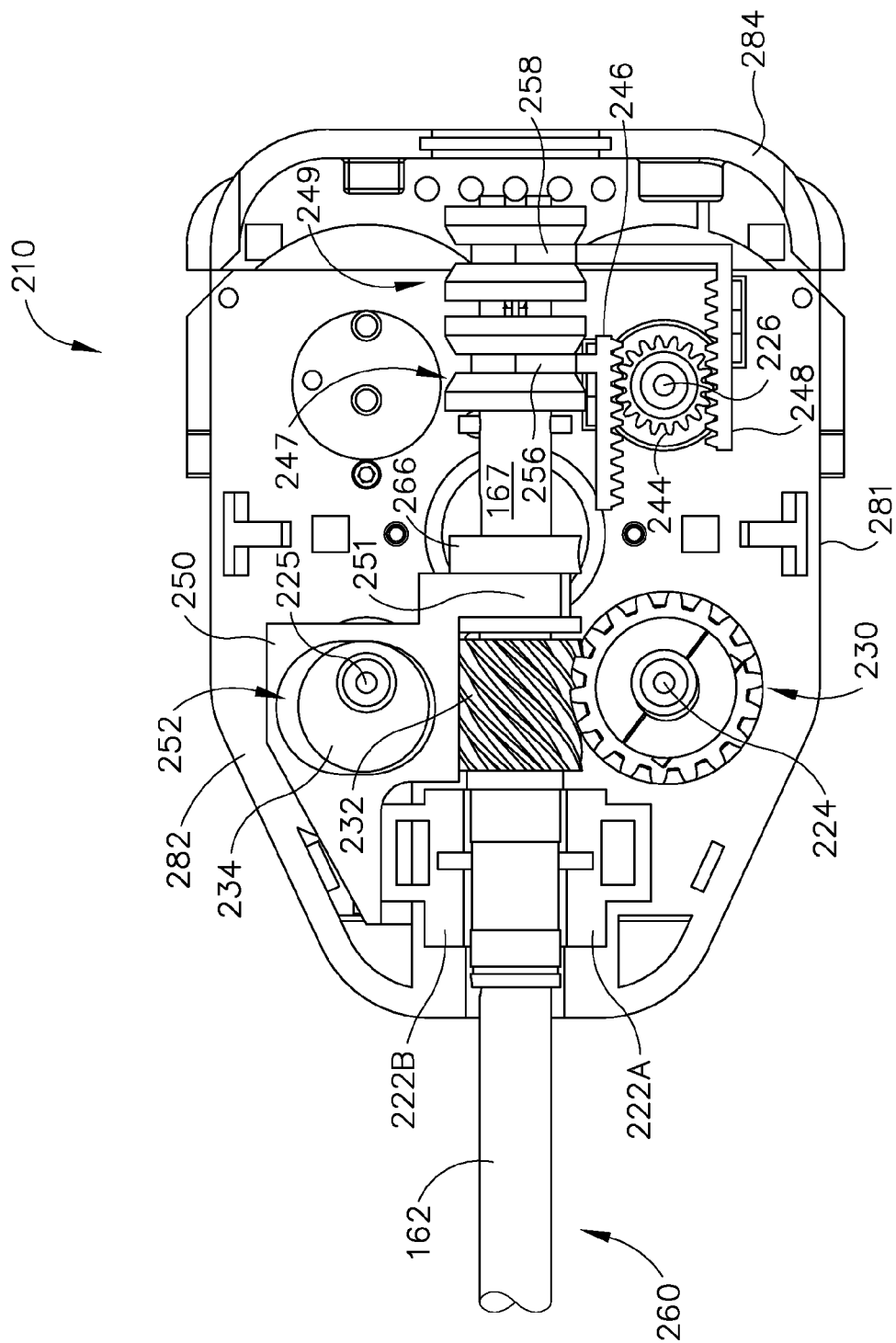
FIG. 18 depicts a top plan view of the proximal portion of the surgical instrument of FIG. 14.

As will be discussed in greater detail below, pivoting base (214) includes three separable sections (281, 282, 284). While not shown, it should be understood that pivoting base (214) may also include one or more electrical contacts and/or other features operable to establish electrical communication with a complementary feature of dock (72). A shaft support structure (222) extends upwardly from pivoting base (214) and provides support to shaft assembly (260) (while still allowing shaft assembly (260) to rotate). Shaft support structure (222) of the present example comprises a first portion (222A) and a second portion (222B). By way of example only, shaft support structure (222) may include a bushing, bearings, and/or other features that facilitate rotation of shaft assembly (260) relative to support structure (222). As shown in FIG. 15, pivoting base (214) further includes three drive discs (220) and one idle disc (223). The drive discs (220) are rotatable within base (214). Drive discs (220) each include a respective pair of unitary pins (221) that couple with complementary recesses (not shown) in corresponding drive elements of dock (72). In some versions, one pin (221) of each pair is closer to the axis of rotation of the corresponding drive disc (220), to ensure proper angular orientation of drive disc (220) relative to the corresponding drive element of dock (72). As best seen in FIGS. 16-18, a drive shaft (224, 225, 226) extends unitarily upwardly from each drive disc (220). As will be described in greater detail below, drive discs (220) are operable to provide independent rotation of shaft assembly (260), bending of articulation section (270), and translation of firing beam (190), through rotation of drive shafts (224, 225, 226). It should be understood that idle disc (223) may be utilized in some versions and various methods of utilization and/or incorporation will be apparent to those of ordinary skill in the art in view of the teachings herein.

Figure 19:
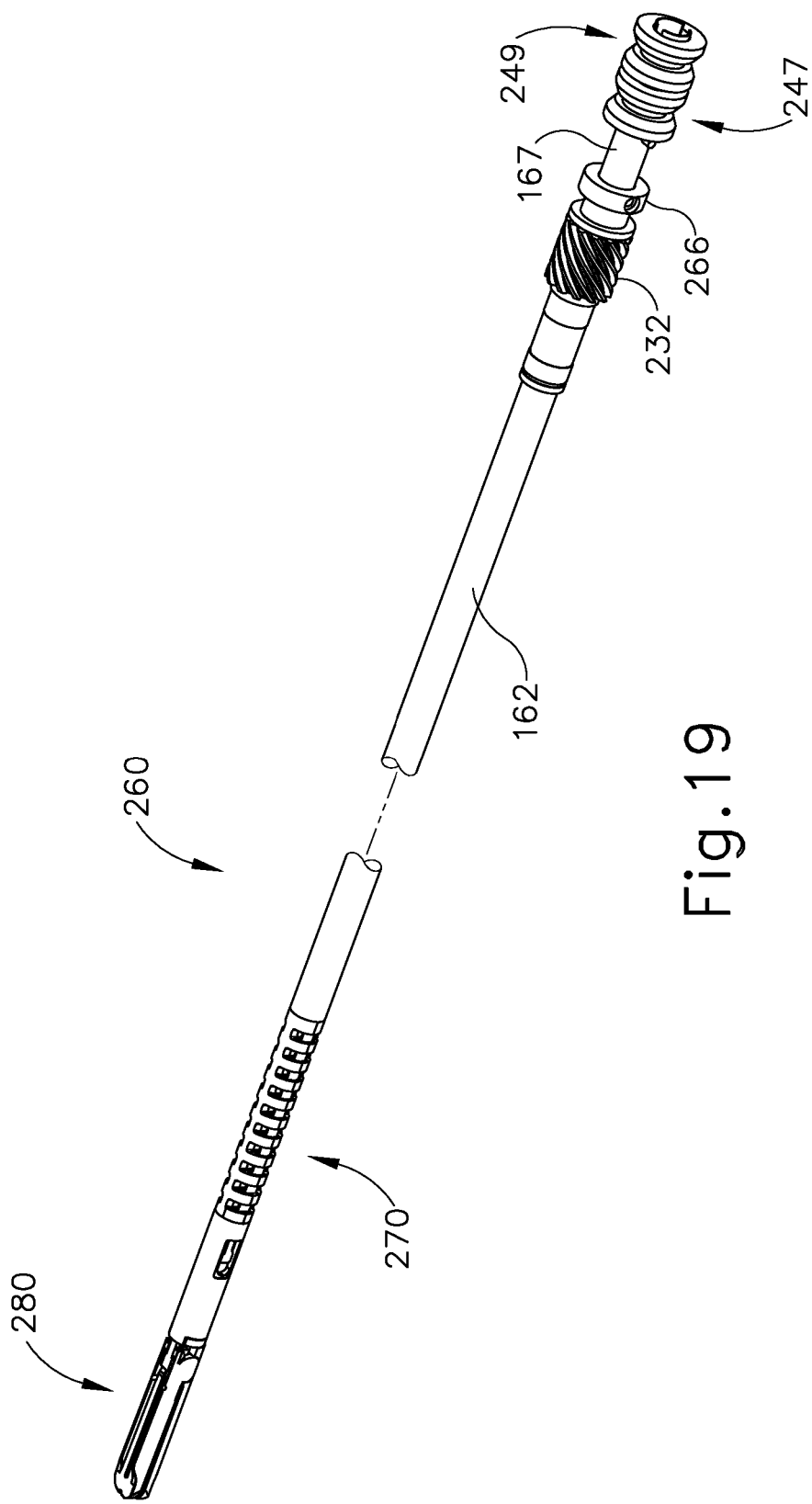
FIG. 19 depicts a perspective view of the shaft assembly of the surgical instrument of FIG. 14.

FIG. 19 shows shaft assembly (260) of the present example in greater detail. Shaft assembly (260) is substantially similar to shaft assembly (160) as discussed above. However, shaft assembly (260) is different in that shaft assembly (260) comprises a first helical gear (232) in place of rotary coupling (164), a firing beam coupling (266) in place of firing beam coupling (166); and additionally a first slide bushing (247) and a second slide bushing (249). As will described in greater detail below, first helical gear (232) is operable to rotate shaft assembly (260) and end effector (280), firing beam coupling (266) is operable to drive firing beam (190), and slide bushings (247, 249) are operable to articulate end effector (280) at articulation section (270).

A. Rotation of Shaft Assembly

As best seen in FIGS. 16-18, a second helical gear (230) is fixedly secured to drive shaft (224), such that rotation of the corresponding drive disc (220) provides rotation of second helical gear (230). Second helical gear (230) meshes with first helical gear (232), which is fixedly secured to an outer sheath (162) of shaft assembly (260). Thus, rotation of second helical gear (230) provides rotation of shaft assembly (260). It should be understood that rotation of second helical gear (230) about a first axis is converted into rotation of first helical gear (232) about a second axis, which is orthogonal to the first axis. A clockwise (CW) rotation of second helical gear (230) (viewed from the proximal end of shaft assembly (260)) results in CW rotation of shaft assembly (260) (viewed from the proximal end). A counter-clockwise (CCW) rotation of second helical gear (230) (viewed from the proximal end of shaft assembly (260)) results in CCW rotation of shaft assembly (260) (viewed from the proximal end).

B. Translation of Firing Beam

As best seen in FIGS. 16-18, an eccentric cam (234) is fixedly secured to drive shaft (225), such that rotation of the corresponding drive disc (220) provides rotation of eccentric cam (234). Eccentric cam (234) is disposed within an oblong recess (252) of a first rack (250). As best seen in FIG. 18, oblong recess (252) is oriented such that rotation of eccentric cam (234) results in translation of first rack (250) along a path that is parallel to a longitudinal axis defined by outer sheath (162) but not transverse to the longitudinal axis defined by outer sheath (162). It should therefore be understood that first rack (250) translates parallel to the longitudinal axis defined by outer sheath (162) in response to rotation of eccentric cam (234). As best seen in FIG. 17, first rack (250) comprises a first fork (251) oriented transverse to the longitudinal axis defined by outer sheath (162). First fork (251) of first rack (250) is coupled to firing beam coupling (266) such that firing beam coupling (266) translates longitudinally with first rack (250). Firing beam coupling (266) is configured to operate substantially similar to firing beam coupling (166) discussed above. Therefore, as discussed above in relation to firing beam coupling (166), translation of firing beam coupling (266) will translate firing beam (190). Thus, it should be understood that rotation of eccentric cam (234) is converted to longitudinal translation of firing beam (190) via first rack (250) and firing beam coupling (266). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (225) via its corresponding drive disc (220). When this rotation is reversed, firing beam (190) retracts proximally, ultimately opening jaws (182, 184) to release tissue.

C. Bending of Articulation Section

With respect to articulation control, FIGS. 16-18 show a spur pinion (244) fixedly secured to drive shaft (226), such that rotation of the corresponding drive disc (220) provides rotation of second spur pinion (244). Spur pinion (244) meshes with a laterally outwardly facing second rack (246). As best seen in FIG. 17, second rack (246) comprises a second fork (256) oriented transverse to the longitudinal axis defined by outer sheath (162). Second fork (256) of second rack (246) is coupled to a first slide bushing (247) such that first slide bushing (247) translates longitudinally with second rack (246). Firing tube (167) is slidably disposed within a central bore of first slide bushing (247) such that first slide bushing (247) is capable of translation along a longitudinal axis defined by firing tube (167). A proximal portion of firing tube (167) includes longitudinally extending slots (137). First slide bushing (247) is fixedly secured to articulation beam (174), which is disposed within a central bore of firing beam (167), via one of the longitudinally extending slots (137). It should therefore be understood that articulation beam (174) will translate distally or proximally in response to rotation of drive shaft (226).

Spur pinion (244) also meshes with a laterally inwardly facing third rack (248). As best seen in FIG. 17, third rack (248) comprises a third fork (258) oriented transverse to the longitudinal axis defined by outer sheath (162). Third fork (258) of third rack (248) is coupled to a second slide bushing (249) such that second slide bushing (249) translates longitudinally with third rack (248). Firing tube (167) is slidably disposed within a central bore of second slide bushing (249) such that second slide bushing (249) is capable of translation along the longitudinal axis defined by firing tube (167). Second slide bushing (249) is fixedly secured to articulation beam (176), which is disposed within a central bore of firing beam (167), via the other one of the longitudinally extending slots (137). It should therefore be understood that articulation beam (176) will translate distally or proximally in response to rotation of drive shaft (226).

Slots (137) are configured to enable free translation of firing tube (167) relative to slide bushings (247,249), to thus enable free actuation of firing beam (190) regardless of the articulation state of articulation section (270). Similarly, slots (137) are configured to enable free translation of slide bushings (247,249) relative to firing tube (167), to thus enable free articulation of articulation section (270) regardless of the longitudinal position of firing beam (190).

As best seen in FIG. 18, second rack (246) and third rack (248) mesh with spur pinion (244) on opposite sides of spur pinion (244) such that rotation of spur pinion (244) will cause second rack (246) and third rack (248) to translate in opposite directions along paths that are parallel to the longitudinal axis defined by outer sheath (162). For instance, a CW rotation of spur pinion (244) (viewed from the top) results in translation of second rack (246) proximally away from end effector (280) and in translation of third rack (248) distally toward end effector (280). On the other hand, a CCW rotation of spur pinion (244) (viewed from the top) results in translation of second rack (246) distally toward end effector (280) and in translation of third rack (248) proximally away from end effector (280).

D. Exemplary Reusable Pivoting Base

Figure 20:
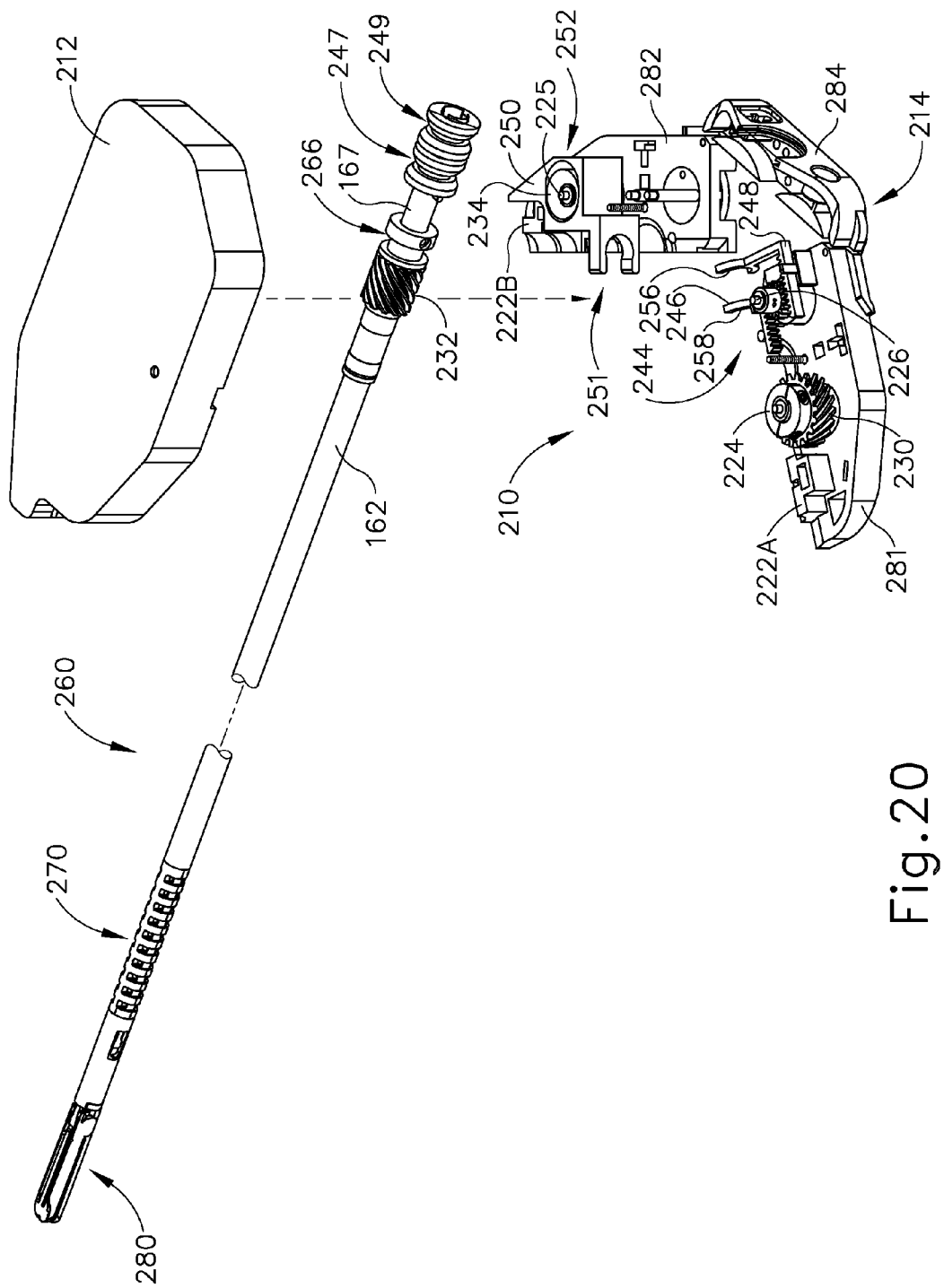
FIG. 20 depicts a perspective view of the shaft assembly of FIG. 19 positioned over an interface assembly of the surgical instrument of FIG. 14, with the interface assembly in an open position.
Figure 23:
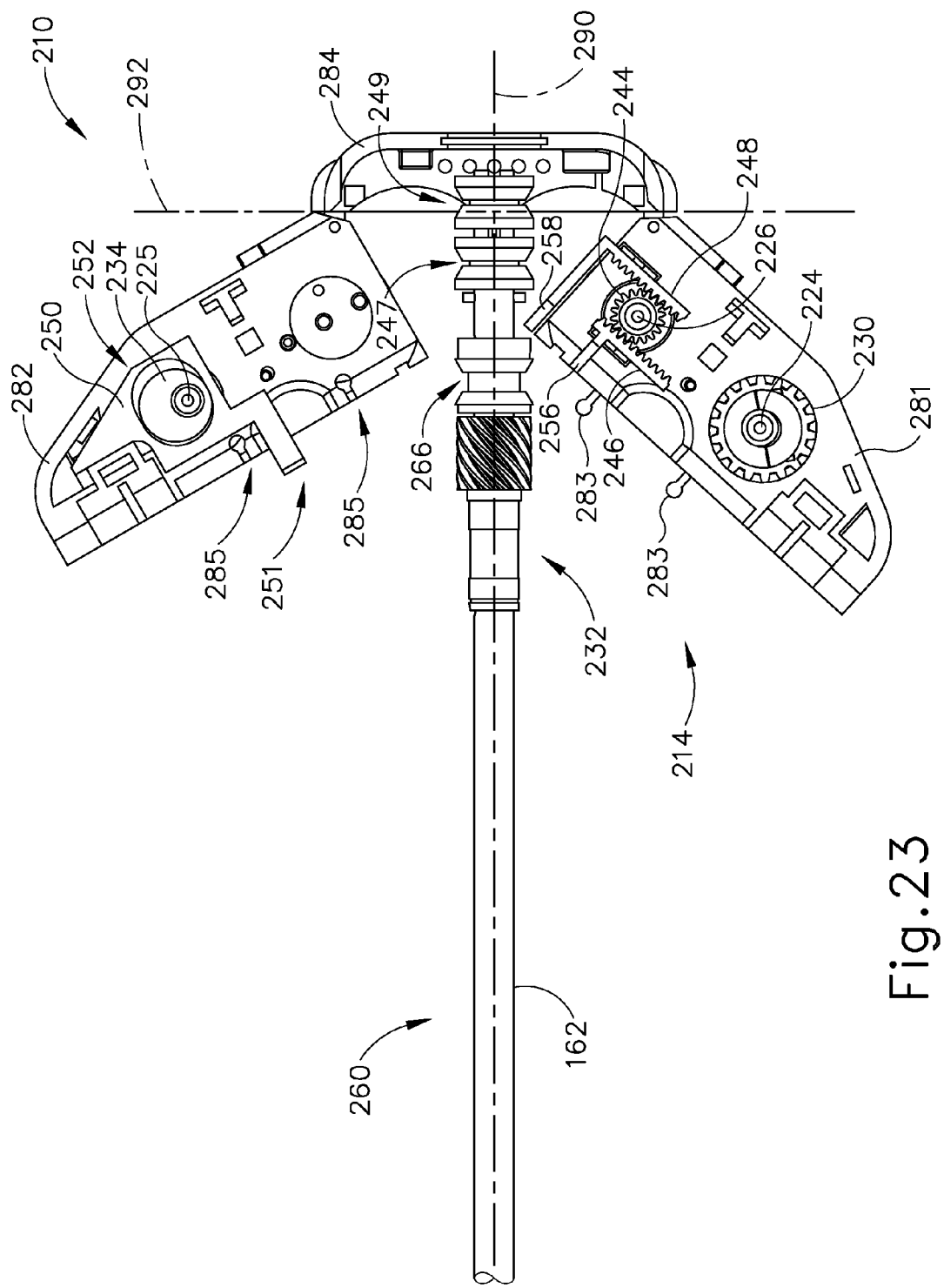
FIG. 23 depicts a top plan view of the interface assembly of FIG. 20 in an open position.
Figure 24:
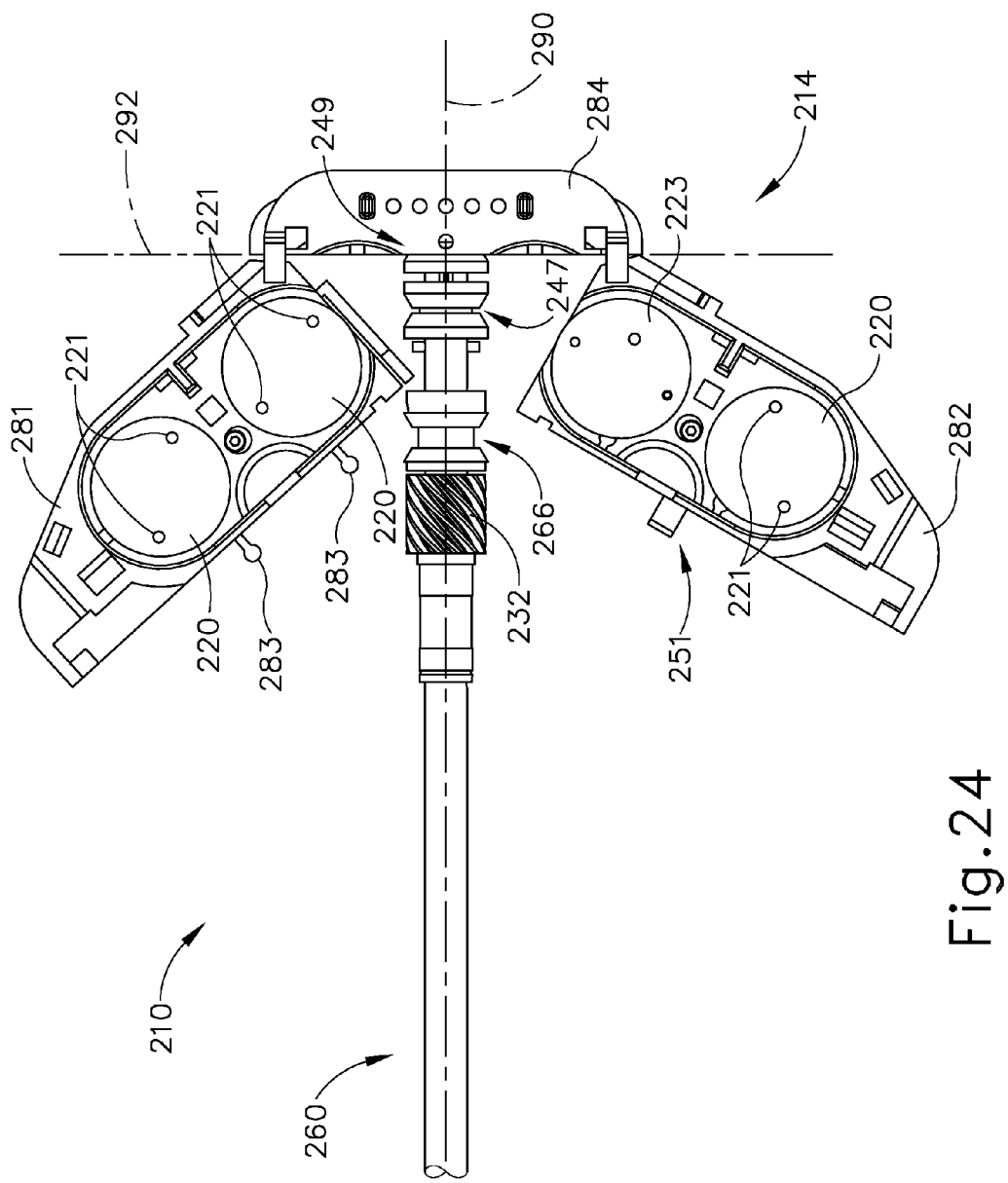
FIG. 24 depicts a bottom plan view of the interface assembly of FIG. 20 in an open position.

In some instances, shaft assembly (260) of the present example is provided as a disposable component while interface assembly (210) is provided as a reusable component. Therefore, among other things, interface assembly (210) is configured to facilitate installation and removal of shaft assembly (260) from surgical instrument (200). As best seen in FIGS. 20 and 23-24, pivoting base (214) of the present example comprises three separable sections (281, 282, 284). A first section (281) and a second section (282) are pivotably coupled to a proximal section (284). Certain drive components discussed above pivot with particular sections (281, 282) of pivoting base (214). For instance, first section (281) comprises first portion (222A) of support structure (222), second helical gear (230), spur pinion (244), second rack (246), third rack (248), drive shaft (224), drive shaft (226), and two of the three drive discs (220) among other components. Second section (282) comprises second portion (222B) of support structure (222), eccentric cam (234), first rack (250), drive shaft (225), idle disc (223) and one of the three drive discs (220) among other components.

In the present example, first section (281) and second section (282) are substantially symmetric portions of pivoting base (214). As best seen in FIG. 23, proximal section (284) is defined by a portion of pivoting base (214) having been severed along a line (292) transverse to the longitudinal axis defined by outer sheath (162) and relative to the proximal end of interface assembly (210). First section (281) and second section (282) are defined by the remaining portion of pivoting base (214) having been divided along a line (290) parallel to the longitudinal axis defined by outer sheath (162). First section (281) and second section (282) are pivotable toward each other. First section (281) and second section (282) pivot about points that are located near the proximal end of base (214) and that are located along a common plane. As seen in FIG. 23, the pivot points for first section (281) and second section (282) are at the same longitudinal position, albeit spaced apart along a common transverse path that is parallel to line (292). Although sections (281, 282, 284) are separated as described above, other suitable ways in which sections (281, 282, 284) may be configured would be apparent to those of ordinary skill in the art in view of the teachings herein.

Figure 21:
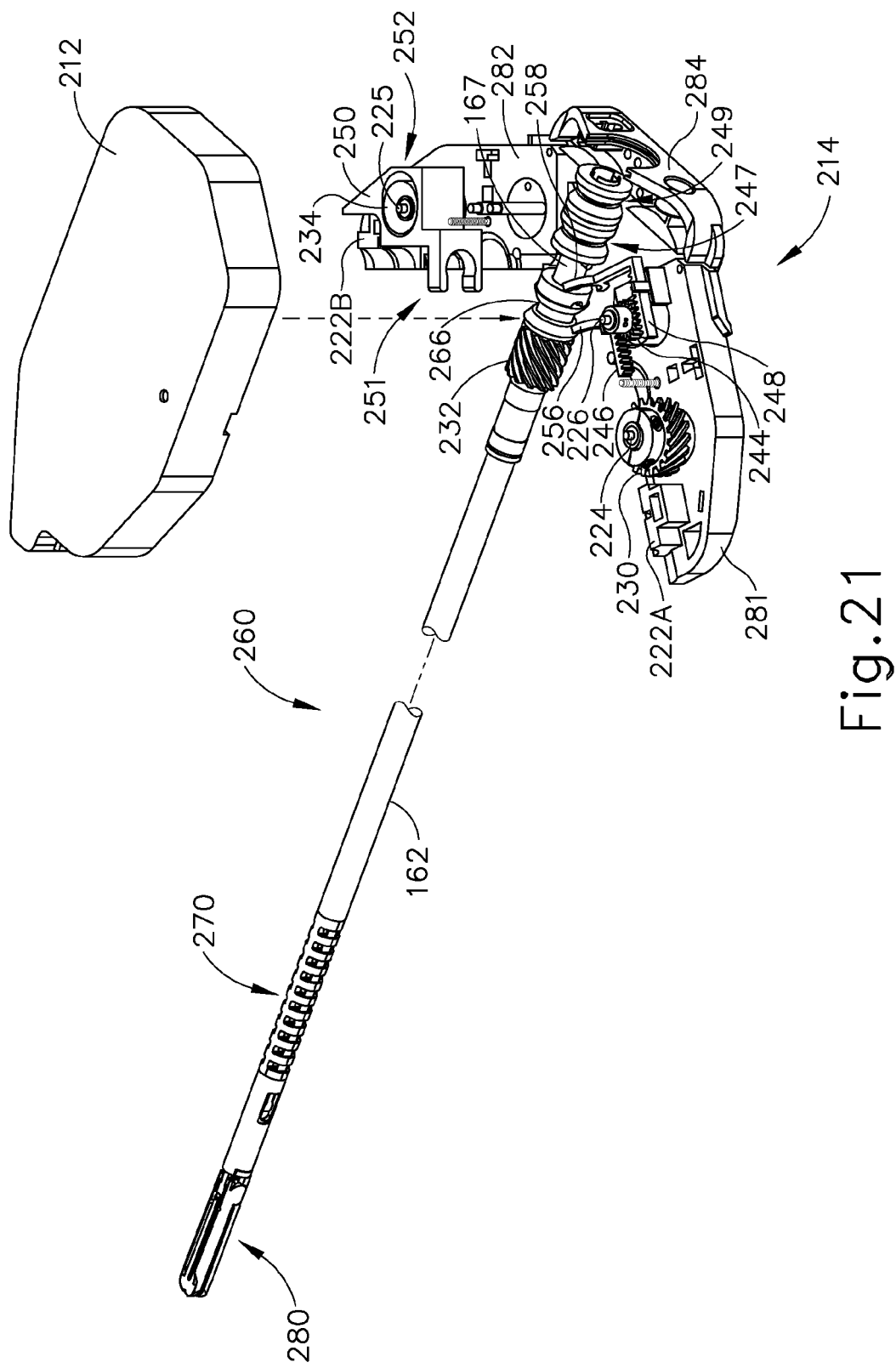
FIG. 21 depicts a perspective view of the shaft assembly of FIG. 19 having been inserted into the interface assembly of FIG. 20, with the interface assembly in an open position.
Figure 22:
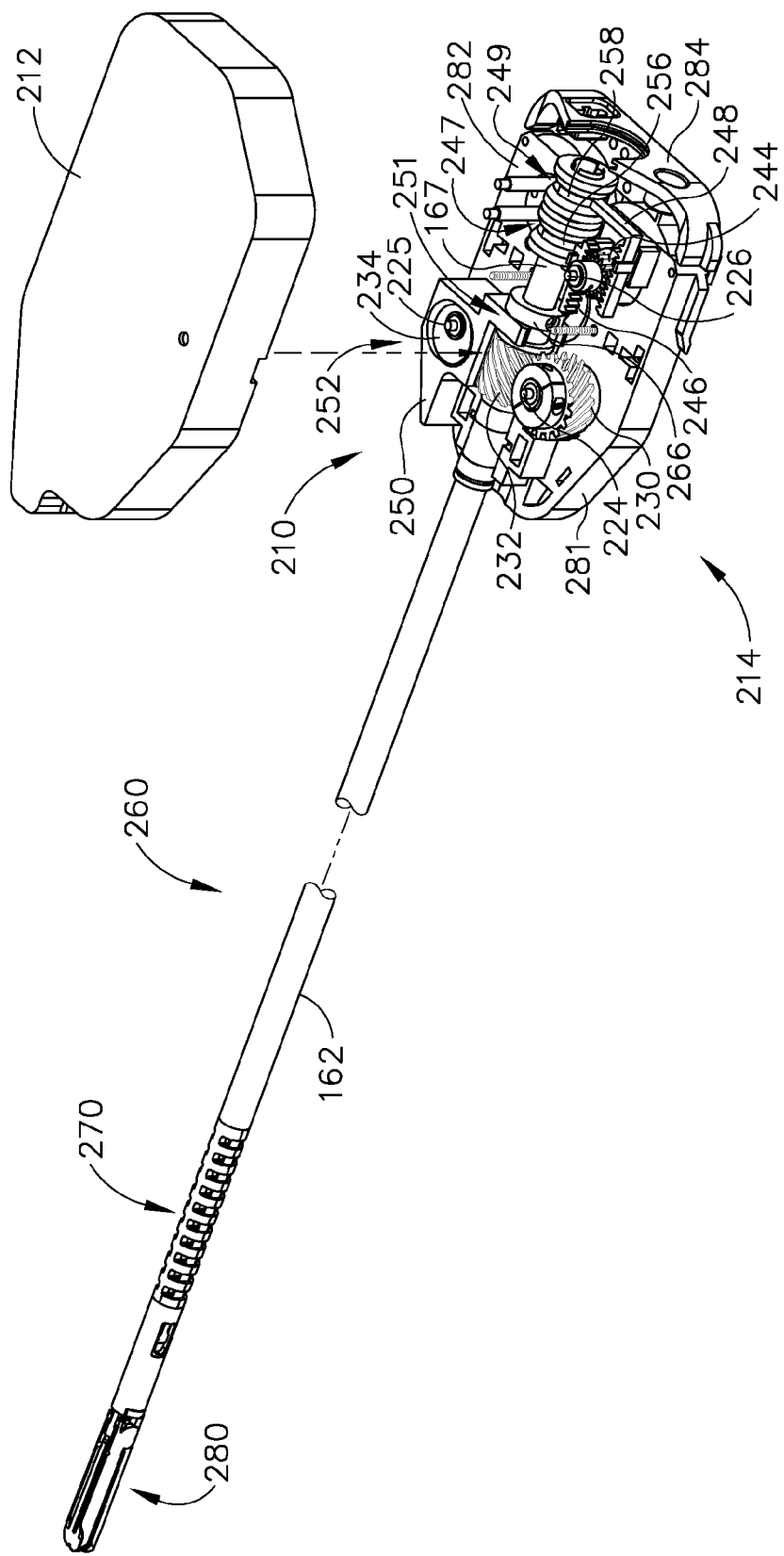
FIG. 22 depicts a perspective view of the shaft assembly of FIG. 19 having been inserted into the interface assembly of FIG. 20, with the interface assembly in a closed position.

FIGS. 20 and 23-24 show sections (281, 282, 284) of interface assembly (210) in an open position. In this open position, the shaft assembly (260) may be inserted into position as shown in the transition from FIG. 20 to FIG. 21. Once shaft assembly (260) is in position, sections (281, 282, 284) of interface assembly (210) are pivoted into a closed position as shown in FIG. 22. During this movement, it is necessary to align first helical gear (232) with second helical gear (230), first rack (250) with firing beam coupling (266), second rack (246) with first slide bushing (247), and third rack (248) with second slide bushing (249) such that the specific couplings discussed above are made as shown in FIG. 22. The transverse configuration of first fork (251) of first rack (250) enables first fork (251) to engage firing beam coupling (266) when sections (281, 282, 284) are closed toward each other. The transverse configuration of second fork (256) of second rack (246) enables second fork (256) to engage first slide bushing (247) when sections (281, 282, 284) are closed toward each other. The transverse configuration of third fork (258) of third rack (248) enables third fork (258) to engage second slide bushing (249) when sections (281, 282, 284) are closed toward each other. As best seen in FIG. 23, a pair of locking features (283) engages a complementary pair of recesses (285) to keep interface assembly in the closed position through a snap fitting. After use, shaft assembly (260) may be removed from surgical instrument (200) by moving interface assembly (210) from the closed position shown in FIG. 22 to the open position of FIG. 20, by pivoting sections (281, 282) outwardly.

E. Exemplary Alternative Reusable Pivoting Base

FIGS. 25-29 show an exemplary alternative interface assembly (310). Interface assembly (310) of this example is substantially similar to interface assembly (210) described above, and can be readily coupled with shaft assembly (260) described above. However, interface assembly (310) of this example is different from interface assembly (210) described above—primarily in that the pivoting sections (380, 382, 384) of base (314) are configured differently from sections (281, 282, 284) of base (214).

Pivoting base (314) of this example comprises three separable sections (380, 382, 384). A first section (380) and a second section (382) are pivotably coupled to a distal section (384). Certain drive components discussed above pivot with particular sections (380, 382, 384) of pivoting base (314). For instance, first section (380) comprises spur pinion (244), second rack (246), third rack (248), drive shaft (226), and one of the three drive discs (220) among other components. Second section (382) comprises eccentric cam (234), first rack (250), drive shaft (225), idle disc (223) and one of the three drive discs (220) among other components. Distal section (384) comprises support structure (222), second helical gear (230), and drive shaft (224) among other components.

Figure 28:
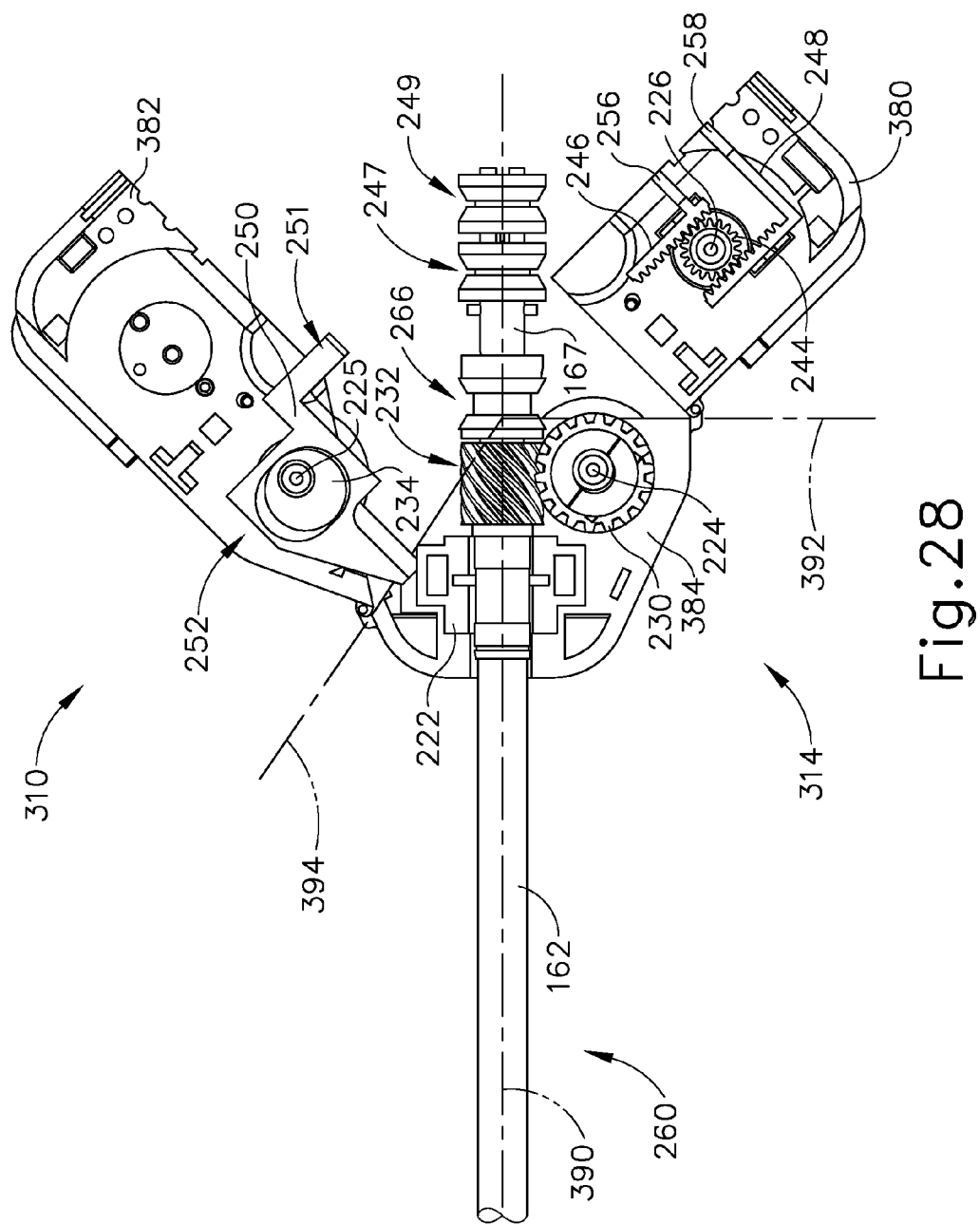
FIG. 28 depicts a top plan view of the interface assembly of FIG. 25 in an open position.
Figure 29:
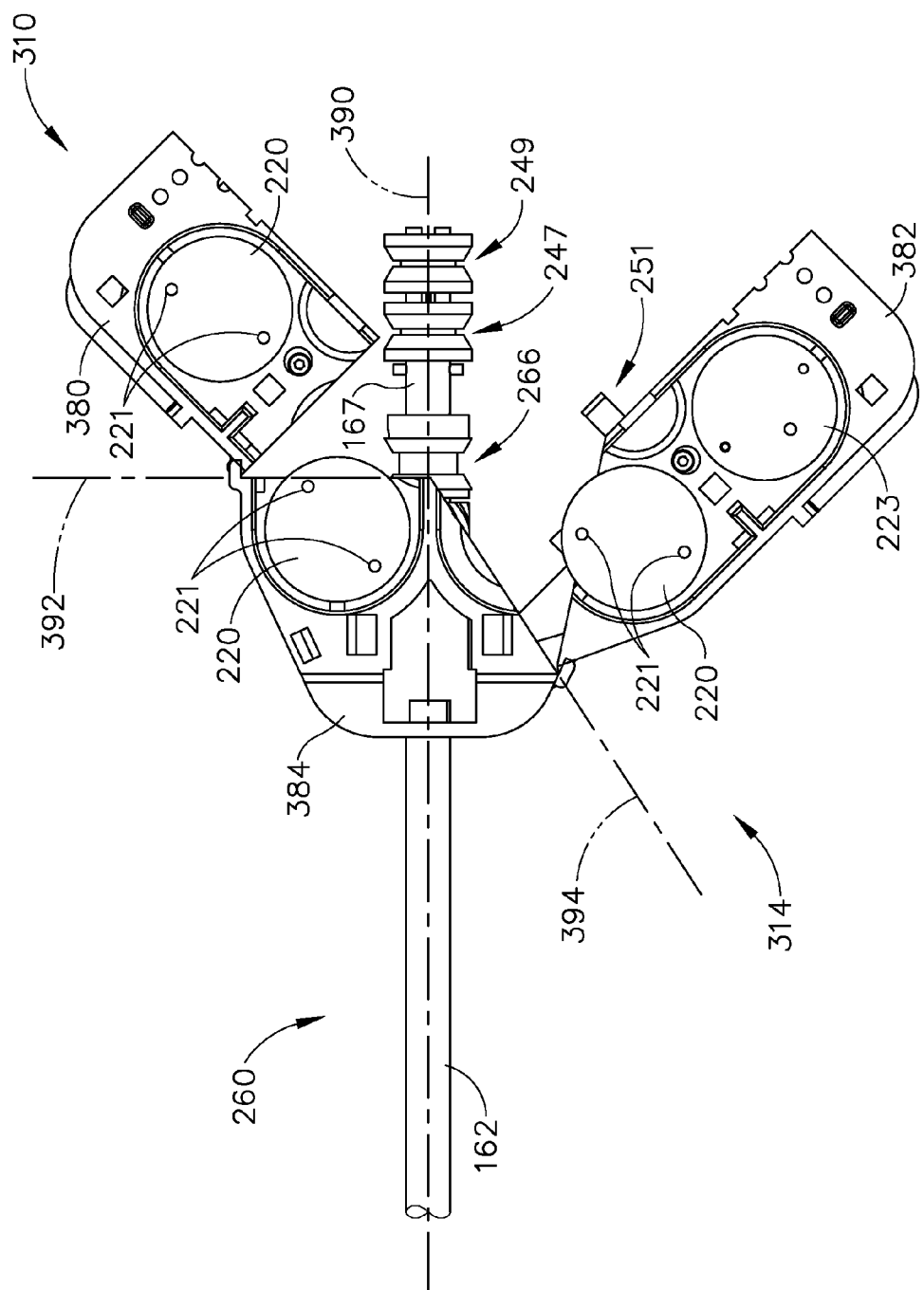
FIG. 29 depicts a bottom plan view of the interface assembly of FIG. 25 in an open position.

In the present example, first section (380) is represents approximately one-quarter of pivoting base (314) and is defined by a portion of pivoting base (314) having been severed along a line (390) parallel to the longitudinal axis defined by outer sheath (162) and a line (392) transverse to the longitudinal axis defined by outer sheath (162). As best seen in FIGS. 28-29, second section (382) is defined by a portion of pivoting base (314) having been severed along line (392) transverse to the longitudinal axis defined by outer sheath (162) and a line (394). As also seen in FIGS. 28-39, distal section (384) is defined by a portion of pivoting base (314) having been severed along line (392) transverse to the longitudinal axis defined by outer sheath (162) and line (394). First section (380) and second section (382) are pivotable toward each other. First section (380) and second section (382) pivot about points that are located near the distal end of base (314) and that are located along a common plane. As seen in FIG. 28, the pivot points for first section (380) and second section (382) are located at staggered longitudinal positions and are laterally spaced apart from each other.

Figure 25:
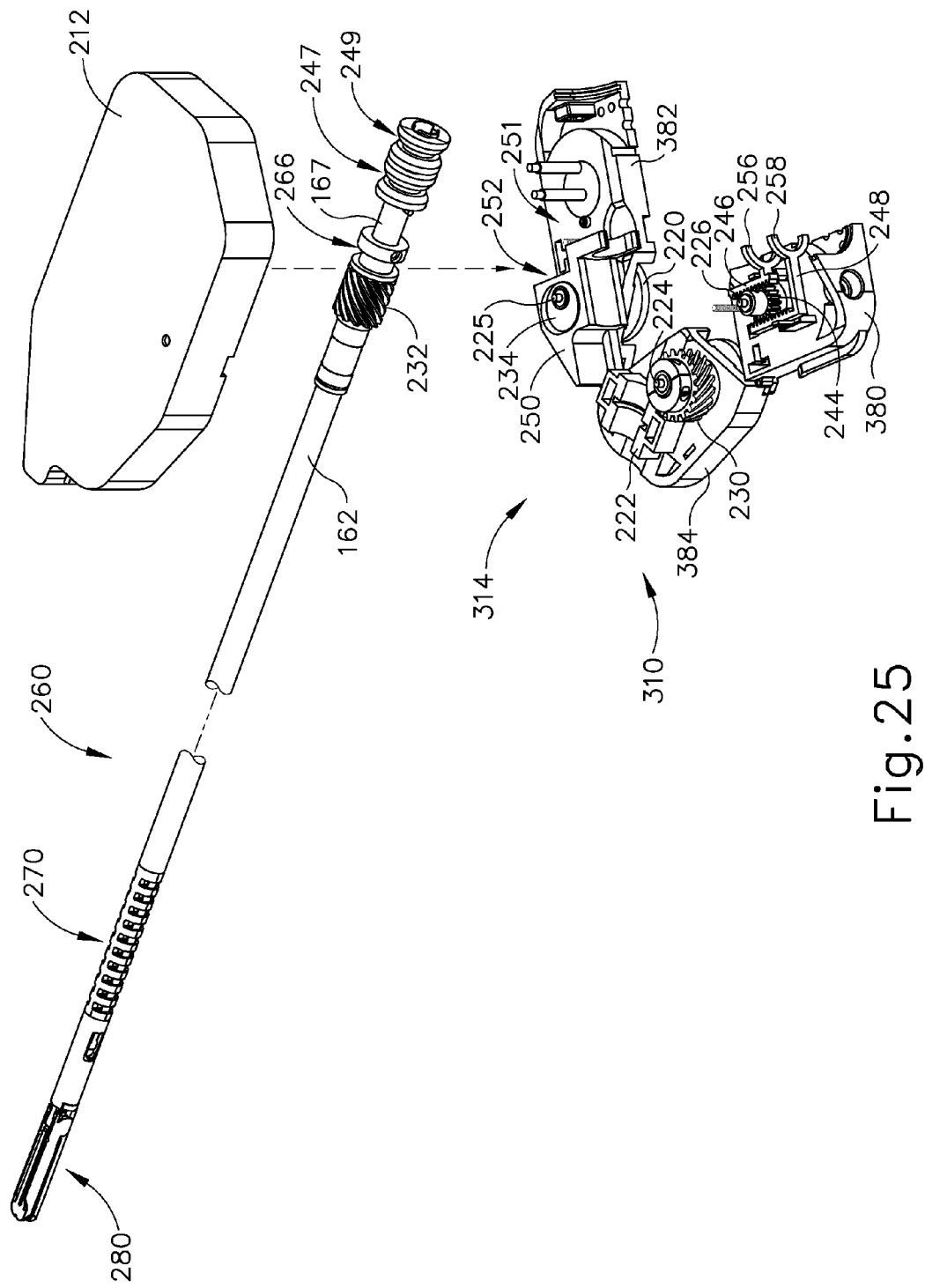
FIG. 25 depicts a perspective view of the shaft assembly of FIG. 19 positioned over an exemplary alternative interface assembly of the surgical instrument of FIG. 14, with the interface assembly in an open position.
Figure 26:
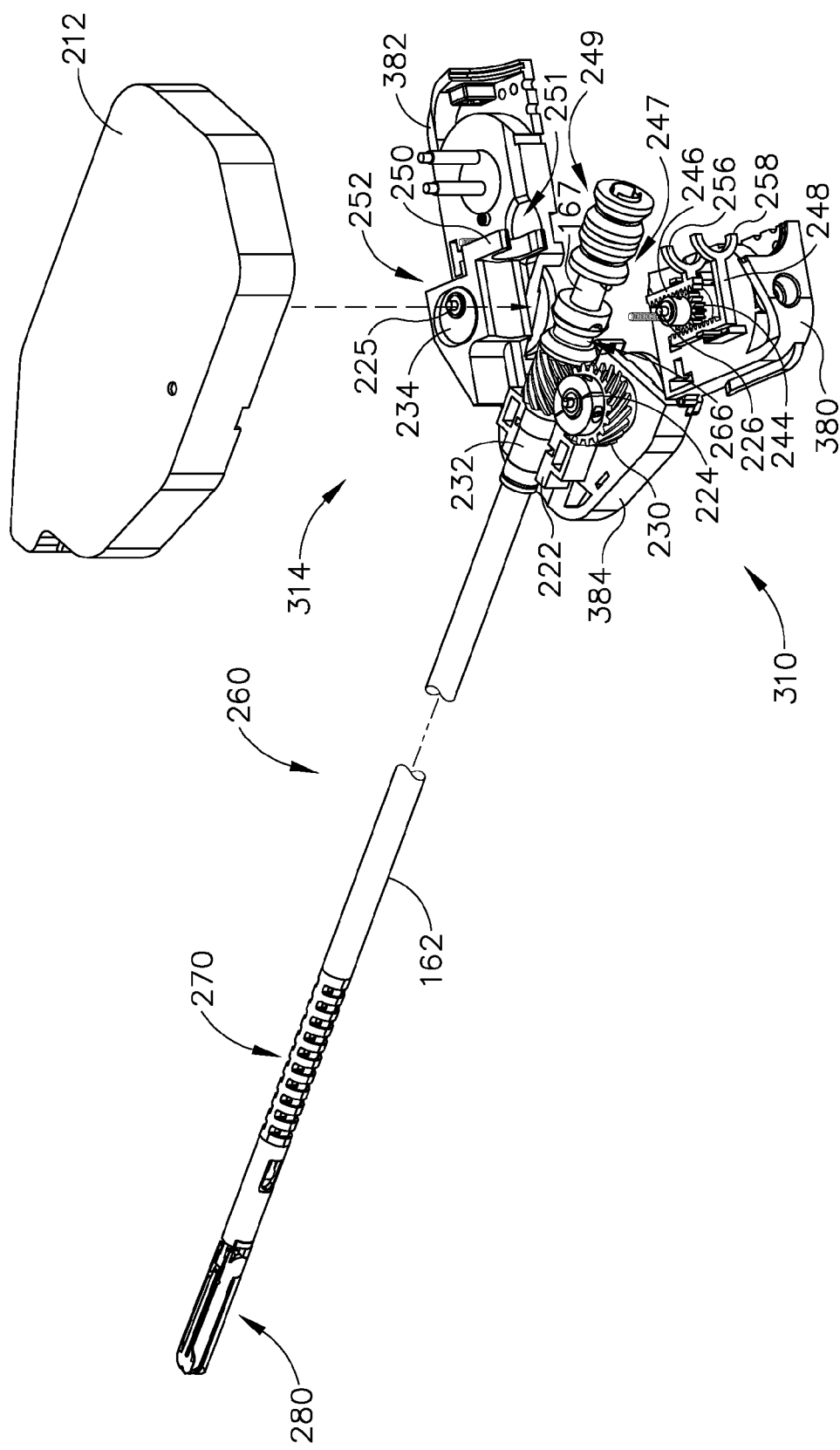
FIG. 26 depicts a perspective view of the shaft assembly of FIG. 19 having been inserted into the interface assembly of FIG. 25, with the interface assembly in an open position.
Figure 27:
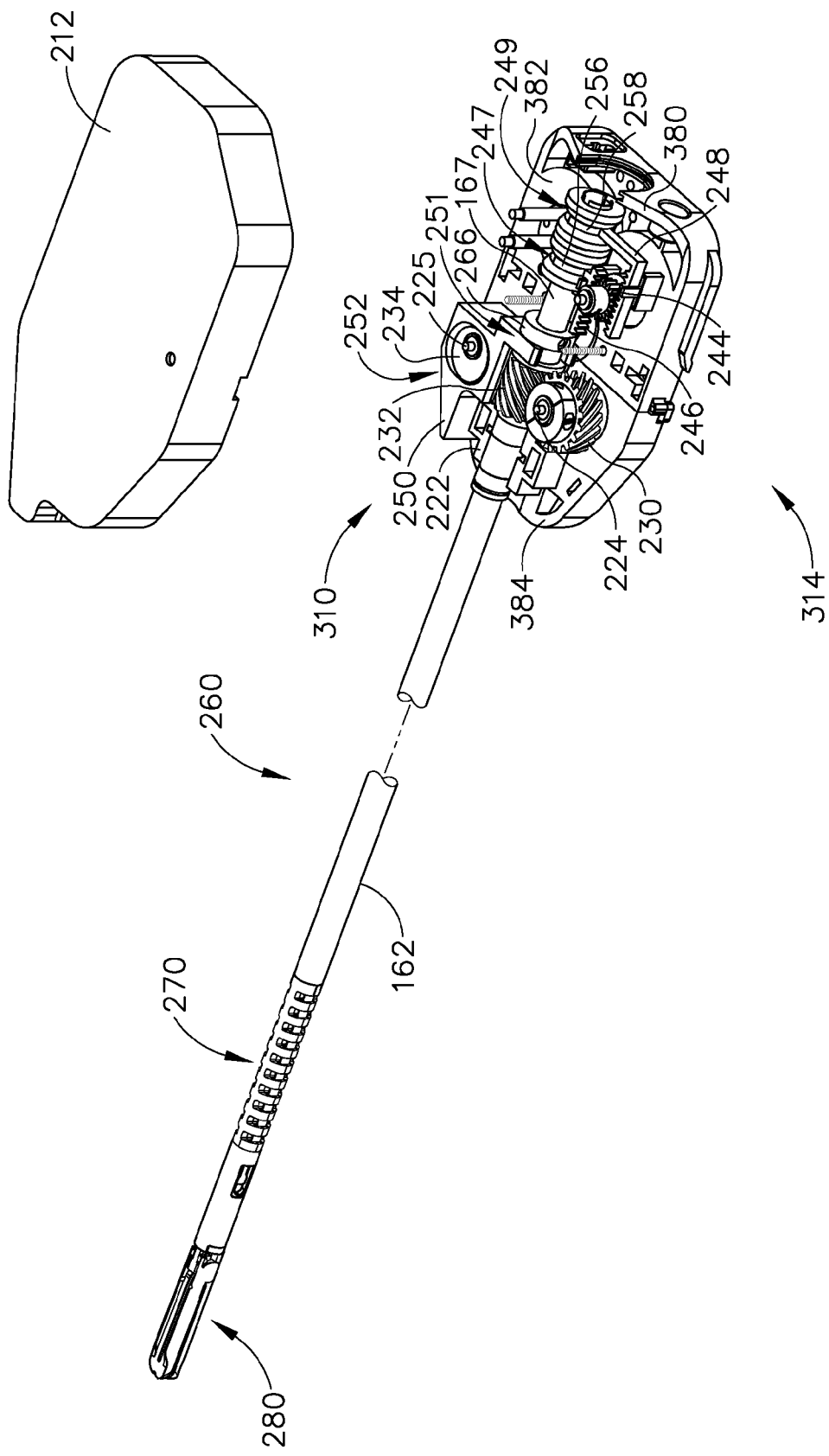
FIG. 27 depicts a perspective view of the shaft assembly of FIG. 19 having been inserted into the interface assembly of FIG. 25, with the interface assembly in a closed position.

FIG. 25 shows sections (380, 382, 384) of base (314) in an open position. In this open position, the shaft assembly (260) may be inserted into position as shown in the transition from FIG. 25 to FIG. 26. Once shaft assembly (260) is in position, sections (380, 382, 384) of base (314) are pivoted into a closed position as shown in FIG. 27. During this movement, it is necessary to align first helical gear (232) with second helical gear (230), fork (251) of first rack (250) with firing beam coupling (266), second rack (246) with first slide bushing (247), and third rack (248) with second slide bushing (249) such that the specific couplings discussed above are made as shown in FIG. 27. The transverse configuration of first fork (251) of first rack (250) enables first fork (251) to engage firing beam coupling (266) when sections (380, 382, 384) are closed toward each other. The transverse configuration of second fork (256) of second rack (246) enables second fork (256) to engage first slide bushing (247) when sections (380, 382, 384) are closed toward each other. The transverse configuration of third fork (258) of third rack (248) enables third fork (258) to engage second slide bushing (249) when sections (380, 382, 384) are closed toward each other. While not shown, this example could utilize locking features similar to those described above and/or any other suitable type of coupling feature to keep interface assembly in the closed position. After use, shaft assembly (260) may be removed from base (314) by moving sections (380, 382) from the closed position shown in FIG. 27 to the open position of FIG. 25, by pivoting sections (380, 382) outwardly.

IV. Miscellaneous

It should be understood that an interface assembly may include an integral power source such as a battery, and that such a battery may provide at least some of any electrical power required to operate the surgical instrument of the interface assembly. In other words, an interface assembly may provide electrical power to one or more components of the associated surgical instrument from a source that is internal to the interface assembly and/or from a source that is external to the interface assembly (e.g., through system (10)). Regardless of where the source is located, the interface assembly may include one or more conductive clips, contacts, and/or other features that provide automatic electrical coupling with the shaft assembly when the shaft assembly is mechanically coupled with the interface assembly. Various suitable ways in which a shaft assembly and an interface assembly may be electrically coupled will be apparent to those of ordinary skill in the art in view of the teachings herein.

Furthermore, an interface assembly may be configured to couple with a variety of types of modular shaft assemblies. Such modular shaft assemblies may provide inter-modality and/or intra-modality variation. Examples of inter-modality variation may include a single interface assembly being able to selectively couple with different shaft assemblies having a variety of end effectors that include staplers, RF electrosurgical features, ultrasonic cutting features, etc. Examples of intra-modality variation may include a single interface assembly being able to selectively couple with different RF electrosurgical shaft assemblies having a variety of end effectors that include straight jaws, curved jaws, etc. Other inter-modality variations and intra-modality variations will be apparent to those of ordinary skill in the art in view of the teachings herein.

In versions where instrument (22) comprises an electrosurgical instrument, system (10) may have a control algorithm whereby articulation drive controls are effectively locked in place when RF electrodes in the end effector of instrument (22) are activated with RF energy. Thus, regardless of whether the end effector is in an articulated position or a straight position when the RF electrodes are activated, a control logic may prevent end effector from being moved from that articulated/straight position when the RF electrodes are activated. Referring back to the example of instrument (100), this may include effectively locking drive shafts (126, 127) when electrodes (186, 187) are activated with RF energy. Referring to the example of instrument (200), this may include effectively locking drive shaft (226) when electrodes in end effector (280) are activated with RF energy. Various suitable ways in which articulation may be selectively locked based on the activation state of RF electrodes will be apparent to those of ordinary skill in the art in view of the teachings herein. It should also be understood that an articulation lockout may be similarly provided when some other kind of activated feature (e.g., an ultrasonic blade, etc.) in an end effector is activated.

Some versions of system (10) may also include one or more features configured to provide sounds generated in vivo during a medical procedure. By way of example only, a microphone may be incorporated into a camera, trocar, and/or instrument (22); and/or a microphone may be provided as a stand-alone instrument. Regardless of how it is incorporated into a particular support structure, the microphone may be positioned inside the patient, at the surgical site near where instrument (22) is operating. In addition or in the alternative, a microphone may be positioned externally, on the patient's skin over the surgical site. Sound captured through either or both kinds of microphones may be amplified and played through speakers, through headphones, and/or through some other kind of device. Such speakers and/or headphones may be located in the same room as the patient. In addition or in the alternative, such speakers and/or headphones may be located at controller (14), such that a remotely operating clinician may hear the in vivo sounds associated with the medical procedure being performed. Of course, these concepts are not limited to a robotic surgical context. These concepts may be readily applied to other laparoscopic surgical contexts as well.

One of ordinary skill in the art will appreciate that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to a surgical stapling instrument, it should be understood that the teachings herein may be combined with the teachings of one or more of the following, the disclosures of all of which are incorporated by reference herein: U.S. Pat. Nos. 7,380,696; 7,404,508; 7,455,208; 7,506,790; 7,549,564; 7,559,450; 7,654,431; 7,780,054; 7,784,662; and/or 7,798,386. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 22, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
(a) an end effector, wherein the end effector comprises:
(i) a first jaw, and
(ii) a second jaw, and wherein the first jaw is movable toward the second jaw to clamp tissue between the first and second jaw;

(b) a shaft assembly, wherein the shaft assembly defines a longitudinal axis, wherein the shaft assembly comprises a distal end and a proximal end, and wherein the end effector is positioned at the distal end of the shaft assembly; and (c) an interface assembly associated with the proximal end of the shaft assembly, wherein the interface assembly comprises:
(i) a first base section, wherein the first base section comprises a first drive component, wherein the first drive component is operable to drive the first jaw of the end effector toward the second jaw of the end effector, and
(ii) a second base section, wherein the second base section comprises a second drive component, wherein the second drive component is operable to actuate at least a portion of the shaft assembly;
wherein the first and second base sections are operable to pivot toward each other to reach a closed position,
wherein the first and second base sections are further operable to pivot away from each other to reach an open position,
wherein at least one of the first base section or the second base section are configured to disengage the shaft assembly when the first and second base sections are in the open position.

2. The apparatus of claim 1, wherein the first and second base sections are configured to engage the shaft assembly when the first and second base sections are in the closed position.

3. The apparatus of claim 1, wherein the shaft assembly is removable from at least one of the first base section or the second base section when the first and second base sections are in the open position.

4. The apparatus of claim 1, wherein the first drive component further comprises an eccentric cam, wherein the eccentric cam is operable to drive the first jaw toward the second jaw.

5. The apparatus of claim 4, wherein the first drive component further comprises a rack, wherein the rack defines an oblong recess, wherein the eccentric cam is disposed within the oblong recess of the rack.

6. The apparatus of claim 5, wherein the oblong recess is configured to provide translation of the rack along a longitudinal axis parallel to the longitudinal axis of the shaft assembly in response to rotation of the eccentric cam.

7. The apparatus of claim 5, wherein the rack of the first drive component further comprises a fork, wherein the fork is configured to engage the shaft assembly when the first and second base sections are in the closed position.

8. The apparatus of claim 1, wherein the shaft assembly further comprises an articulation section, wherein the articulation section is operable to deflect at least part of the end effector away from the longitudinal axis.

9. The apparatus of claim 8, wherein the second drive component comprises a spur pinion, wherein the spur pinion is fixedly secured to the second rotatable member, wherein the spur pinion is operable to drive articulation of the articulation section.

10. The apparatus of claim 9, wherein the second drive component further comprises a rack configured to mesh with the spur pinion.

11. The apparatus of claim 10, wherein the rack of the second drive component further comprises a fork configured to engage the shaft assembly when the first and second base sections are in the closed position.

12. The apparatus of claim 9, wherein the shaft assembly further comprises:
(i) a first articulation band, wherein the first articulation band is coupled to a first bushing, and wherein the first bushing is configured to translate parallel to the longitudinal axis of the shaft assembly, and
(ii) a second articulation band, wherein the second articulation band is coupled to a second bushing, and wherein the second bushing is configured to translate parallel to the longitudinal axis of the shaft assembly.

13. The apparatus of claim 1, wherein the second drive component comprises an idler component.

14. The apparatus of claim 1, wherein the second drive component is configured to rotate one or both of the shaft assembly or the end effector about the longitudinal axis of the shaft assembly.

15. The apparatus of claim 14, wherein the second drive component comprises a first helical gear.

16. The apparatus of claim 15, wherein the shaft assembly comprises a second helical gear configured to mesh with the first helical gear when the first and second base sections are in the closed position.

17. The apparatus of claim 1, wherein the interface assembly further comprises a locking feature configured to secure the first and second base sections relative to each other.

18. An apparatus for operating on tissue, the apparatus comprising:
(a) an end effector wherein the end effector comprises:
(i) a first jaw, and
(ii) a second jaw, and wherein the first jaw is movable toward the second jaw to clamp tissue between the first and second jaw;
(b) a shaft assembly, wherein the shaft assembly defines a longitudinal axis, wherein the shaft assembly comprises a proximal end and a distal end, and wherein the end effector is positioned at the distal end of the shaft assembly; and
(c) an interface assembly associated with the proximal end of the shaft assembly, wherein the interface assembly comprises:
(i) a first base section comprising a first actuator, and
(ii) a second base section comprising a second actuator,
wherein the first and second base sections are operable to pivot toward each other from an open position to a closed position,
wherein at least one of the first base section or the second base section are configured to disengage the shaft assembly when the first and second base sections are in the open position, wherein the first actuator is configured to actuate a first portion of the shaft assembly or end effector when the interface assembly is in the closed position, wherein the second actuator is configured to actuate a second portion of the shaft assembly or end effector when the interface assembly is in the closed position.

19. An apparatus for operating on tissue, the apparatus comprising:
(a) an end effector wherein the end effector comprises:
(i) a first jaw, and
(ii) a second jaw, and wherein the first jaw is movable toward the second jaw to clamp tissue between the first and second jaw;
(b) a shaft assembly, wherein the shaft assembly defines a longitudinal axis, wherein the shaft assembly comprises a distal end, a proximal end, a first interface feature configured to actuate the end effector, and a second interface feature configured to actuate the end effector, wherein the end effector is positioned at the distal end of the shaft assembly; and (c) an interface assembly associated with the proximal end of the shaft assembly, wherein the interface assembly comprises:

(i) a first base section, and (ii) a second base section, wherein the first and second base sections are operable to pivot toward each other to reach a closed position, wherein the first base section is configured to drive the first interface feature when the interface assembly is in the closed position, wherein the second base section is configured to drive the second interface feature when the interface assembly is in the closed position, wherein the first and second base sections are further operable to pivot away from each other to reach an open position, wherein the first and second base sections are configured to fix the shaft assembly relative to the interface assembly along the longitudinal axis when the first and second base sections are in the closed position.

* * * * *